(12) United States Patent
Satish et al.

(10) Patent No.: US 10,706,541 B2
(45) Date of Patent: *Jul. 7, 2020

(54) SYSTEM AND METHOD FOR ESTIMATING A QUANTITY OF A BLOOD COMPONENT IN A FLUID CANISTER

(71) Applicant: Gauss Surgical, Inc., Menlo Park, CA (US)

(72) Inventors: Siddarth Satish, Cupertino, CA (US); Ali Zandifar, San Francisco, CA (US); Kevin J. Miller, Mountain View, CA (US)

(73) Assignee: Gauss Surgical, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/392,345

(22) Filed: Apr. 23, 2019

(65) Prior Publication Data
US 2019/0385305 A1 Dec. 19, 2019

Related U.S. Application Data

(63) Continuation of application No. 15/416,986, filed on Jan. 26, 2017, now Pat. No. 10,282,839, which is a
(Continued)

(51) Int. Cl.
*A61B 5/00* (2006.01)
*G06T 7/00* (2017.01)
(Continued)

(52) U.S. Cl.
CPC ............ *G06T 7/0012* (2013.01); *G01F 22/00* (2013.01); *G01F 23/292* (2013.01); *G01N 21/25* (2013.01);
(Continued)

(58) Field of Classification Search
CPC ............ A61M 1/024; A61F 2/00; A61B 5/00
(Continued)

(56) References Cited

U.S. PATENT DOCUMENTS 2,707,955 A 5/1955 Borden
3,182,252 A 5/1965 van den Berg
(Continued)

FOREIGN PATENT DOCUMENTS

CA 2870635 A1 10/2013
CN 101505813 A 8/2009
(Continued)

OTHER PUBLICATIONS

ACOG (2012). "Optimizing protocols in obstetrics," Series 2, 25 total pages.
(Continued)

*Primary Examiner* — Abolfazl Tabatabai
(74) *Attorney, Agent, or Firm* — Schwegman Lundberg & Woessner, P.A.

(57) ABSTRACT

A variation of a method for estimating a quantity of a blood component in a fluid canister includes: within an image of a canister, identifying a reference marker on the canister; selecting an area of the image based on the reference marker; correlating a portion of the selected area with a fluid level within the canister; estimating a volume of fluid within the canister based on the fluid level; extracting a feature from the selected area; correlating the extracted featured with a concentration of a blood component within the canister; and estimating a quantity of the blood component within the canister based on the estimated volume and the concentration of the blood component within the canister.

1 Claim, 9 Drawing Sheets

Related U.S. Application Data continuation of application No. 14/876,628, filed on Oct. 6, 2015, now Pat. No. 9,595,104, which is a continuation of application No. 14/613,807, filed on Feb. 4, 2015, now Pat. No. 9,171,368, which is a continuation of application No. 13/738,919, filed on Jan. 10, 2013, now Pat. No. 8,983,167.

(60) Provisional application No. 61/722,780, filed on Nov. 5, 2012, provisional application No. 61/703,179, filed on Sep. 19, 2012, provisional application No. 61/646,822, filed on May 14, 2012.

(51) Int. Cl.
*G01N 21/90* (2006.01)
*G06T 7/70* (2017.01)
*G06T 7/90* (2017.01)
*G01N 21/25* (2006.01)
*G01N 21/84* (2006.01)
*G01F 23/292* (2006.01)
*G01F 22/00* (2006.01)
*G01N 33/49* (2006.01)

(52) U.S. Cl.
CPC ............ *G01N 21/84* (2013.01); *G01N 21/90* (2013.01); *G01N 33/49* (2013.01); *G06T 7/70* (2017.01); *G06T 7/90* (2017.01); *G06T 2207/10024* (2013.01); *G06T 2207/30004* (2013.01)

(58) Field of Classification Search
USPC ......................................... 382/128
See application file for complete search history.

(56) References Cited

U.S. PATENT DOCUMENTS

| | | |
|---|---|---|
| 3,199,507 A | 8/1965 | Kamm |
| 3,367,431 A | 2/1968 | Baker |
| 3,646,938 A | 3/1972 | Haswell |
| 3,832,135 A | 8/1974 | Drozdowski et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,190,153 A | 2/1980 | Olsen |
| 4,244,369 A | 1/1981 | McAvinn et al. |
| 4,295,537 A | 10/1981 | McAvinn et al. |
| 4,313,292 A | 2/1982 | McWilliams |
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,009,275 A | 4/1991 | Sheehan |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 6/1992 | Manion et al. |
| 5,190,059 A | 3/1993 | Fabian et al. |
| 5,227,765 A | 7/1993 | Ishizuka et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon et al. |
| 5,369,713 A | 11/1994 | Schwartz et al. |
| 5,443,082 A | 8/1995 | Mewburn |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,640,130 B1 | 10/2003 | Freeman et al. |
| 6,641,039 B2 | 11/2003 | Southard |
| 6,699,231 B1 | 3/2004 | Sterman et al. |
| 6,728,561 B2 | 4/2004 | Smith et al. |
| 6,730,054 B2 | 5/2004 | Pierce et al. |
| 6,763,148 B1 | 7/2004 | Sternberg et al. |
| 6,777,623 B2 | 8/2004 | Ballard |
| 6,781,067 B2 | 8/2004 | Montagnino |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,255,003 B2 | 8/2007 | Schneiter |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 * | 6/2008 | Ghajar .................. A61B 3/113 351/201 |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart |
| 7,708,700 B2 | 5/2010 | Ghajar |
| 7,711,403 B2 * | 5/2010 | Jay ...................... A61B 5/0059 356/456 |
| 7,749,217 B2 | 7/2010 | Podhajsky |
| 7,795,491 B2 | 9/2010 | Stewart et al. |
| 7,819,818 B2 | 10/2010 | Ghajar |
| 7,872,201 B1 | 1/2011 | Whitney |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,241,238 B2 | 8/2012 | Hiruma et al. |
| 8,279,068 B2 | 10/2012 | Morris et al. |
| 8,374,397 B2 | 2/2013 | Shpunt et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,639,226 B2 | 1/2014 | Hutchings et al. |
| 8,693,753 B2 | 4/2014 | Nakamura |
| 8,704,178 B1 | 4/2014 | Pollock et al. |
| 8,768,014 B2 | 7/2014 | Du et al. |
| 8,792,693 B2 | 7/2014 | Satish et al. |
| 8,823,776 B2 | 9/2014 | Tian et al. |
| 8,897,523 B2 | 11/2014 | Satish et al. |

(56) References Cited

U.S. PATENT DOCUMENTS

| | | | |
|---|---|---|---|
| 8,983,167 B2 | 3/2015 | Satish et al. | |
| 8,985,446 B2 | 3/2015 | Fleck et al. | |
| 9,047,663 B2 | 6/2015 | Satish et al. | |
| 9,171,368 B2 | 10/2015 | Satish et al. | |
| 9,347,817 B2 | 5/2016 | Pollock et al. | |
| 9,594,983 B2* | 3/2017 | Alattar | G06F 21/16 |
| 9,595,104 B2 | 3/2017 | Satish et al. | |
| 9,646,375 B2* | 5/2017 | Satish | G06T 7/0012 |
| 9,652,655 B2 | 5/2017 | Satish et al. | |
| 9,824,441 B2 | 11/2017 | Satish et al. | |
| 9,936,906 B2 | 4/2018 | Satish et al. | |
| 10,282,839 B2 | 5/2019 | Satish et al. | |
| 2003/0069509 A1 | 4/2003 | Matzinger et al. | |
| 2003/0095197 A1 | 5/2003 | Wheeler et al. | |
| 2003/0130596 A1 | 7/2003 | Von Der Goltz | |
| 2004/0031626 A1 | 2/2004 | Morris et al. | |
| 2004/0129678 A1 | 7/2004 | Crowley et al. | |
| 2005/0051466 A1 | 3/2005 | Carter et al. | |
| 2005/0163354 A1 | 7/2005 | Ziegler | |
| 2005/0265996 A1 | 12/2005 | Lentz | |
| 2006/0058593 A1 | 3/2006 | Drinan et al. | |
| 2006/0178578 A1 | 8/2006 | Tribble et al. | |
| 2006/0224086 A1 | 10/2006 | Harty | |
| 2007/0004959 A1 | 1/2007 | Carrier et al. | |
| 2007/0024946 A1 | 2/2007 | Panasyuk et al. | |
| 2007/0108129 A1 | 5/2007 | Mori et al. | |
| 2007/0243137 A1 | 10/2007 | Hainfeld | |
| 2007/0287182 A1 | 12/2007 | Morris et al. | |
| 2008/0029416 A1 | 2/2008 | Paxton | |
| 2008/0030303 A1 | 2/2008 | Kobren et al. | |
| 2008/0045845 A1 | 2/2008 | Pfeiffer et al. | |
| 2008/0194906 A1 | 8/2008 | Mahony et al. | |
| 2009/0076470 A1 | 3/2009 | Ryan | |
| 2009/0080757 A1 | 3/2009 | Roger et al. | |
| 2009/0257632 A1 | 10/2009 | Lalpuria et al. | |
| 2009/0310123 A1 | 12/2009 | Thomson | |
| 2009/0317002 A1 | 12/2009 | Dein | |
| 2010/0003714 A1 | 1/2010 | Bachur | |
| 2010/0007727 A1 | 1/2010 | Torre-Bueno | |
| 2010/0025336 A1 | 2/2010 | Carter et al. | |
| 2010/0027868 A1 | 2/2010 | Kosaka et al. | |
| 2010/0066996 A1 | 3/2010 | Kosaka et al. | |
| 2010/0087770 A1 | 4/2010 | Bock | |
| 2010/0150759 A1 | 6/2010 | Mazur et al. | |
| 2010/0152563 A1 | 6/2010 | Turner et al. | |
| 2010/0280117 A1 | 11/2010 | Patrick et al. | |
| 2011/0066182 A1 | 3/2011 | Falus | |
| 2011/0118647 A1 | 5/2011 | Paolini et al. | |
| 2011/0192745 A1 | 8/2011 | Min | |
| 2011/0196321 A1 | 8/2011 | Wudyka | |
| 2011/0200239 A1 | 8/2011 | Levine et al. | |
| 2011/0275957 A1 | 11/2011 | Bhandari | |
| 2011/0305376 A1 | 12/2011 | Neff | |
| 2011/0316973 A1 | 12/2011 | Miller et al. | |
| 2012/0000297 A1 | 1/2012 | Hashizume et al. | |
| 2012/0064132 A1 | 3/2012 | Aizawa et al. | |
| 2012/0065482 A1 | 3/2012 | Robinson et al. | |
| 2012/0106811 A1 | 5/2012 | Chen et al. | |
| 2012/0127290 A1 | 5/2012 | Tojo et al. | |
| 2012/0210778 A1 | 8/2012 | Palmer et al. | |
| 2012/0257188 A1 | 10/2012 | Yan et al. | |
| 2012/0262704 A1 | 10/2012 | Zahniser et al. | |
| 2012/0309636 A1 | 12/2012 | Gibbons et al. | |
| 2012/0327365 A1 | 12/2012 | Makihira | |
| 2012/0330117 A1 | 12/2012 | Grudic et al. | |
| 2013/0010094 A1 | 1/2013 | Satish et al. | |
| 2013/0011031 A1 | 1/2013 | Satish et al. | |
| 2013/0011042 A1 | 1/2013 | Satish et al. | |
| 2013/0034908 A1 | 2/2013 | Barstis et al. | |
| 2013/0088354 A1 | 4/2013 | Thomas | |
| 2013/0094996 A1 | 4/2013 | Janssenswillen | |
| 2013/0170729 A1 | 7/2013 | Wardlaw et al. | |
| 2013/0301901 A1 | 11/2013 | Satish et al. | |
| 2013/0303870 A1 | 11/2013 | Satish et al. | |
| 2013/0308852 A1 | 11/2013 | Hamsici et al. | |
| 2014/0079297 A1 | 3/2014 | Tadayon et al. | |
| 2014/0128838 A1 | 5/2014 | Satish et al. | |
| 2014/0207091 A1 | 7/2014 | Heagle et al. | |
| 2014/0294237 A1 | 10/2014 | Litvak et al. | |
| 2014/0330094 A1 | 11/2014 | Pacione et al. | |
| 2015/0046124 A1 | 2/2015 | Bhavaraju et al. | |
| 2015/0154751 A1 | 6/2015 | Satish et al. | |
| 2015/0294460 A1 | 10/2015 | Satish et al. | |
| 2015/0310634 A1 | 10/2015 | Babcock et al. | |
| 2016/0027173 A1 | 1/2016 | Satish et al. | |
| 2016/0069743 A1 | 3/2016 | McQuilkin et al. | |
| 2016/0123998 A1 | 5/2016 | MacIntyre et al. | |
| 2016/0331248 A1 | 11/2016 | Satish et al. | |
| 2016/0331282 A1 | 11/2016 | Satish et al. | |
| 2017/0011276 A1 | 1/2017 | Mehring et al. | |
| 2017/0023446 A1 | 1/2017 | Rietveld et al. | |
| 2017/0186160 A1 | 6/2017 | Satish et al. | |
| 2017/0351894 A1 | 12/2017 | Satish et al. | |
| 2017/0352152 A1 | 12/2017 | Satish et al. | |
| 2018/0199827 A1 | 7/2018 | Satish et al. | |
| 2019/0008427 A1 | 1/2019 | Satish et al. | |

FOREIGN PATENT DOCUMENTS

| | | |
|---|---|---|
| CN | 101809432 A | 8/2010 |
| CN | 102216161 A | 10/2011 |
| CN | 109738621 A | 5/2019 |
| EP | 2850559 A1 | 3/2015 |
| JP | 59161801 U | 10/1984 |
| JP | S-59-161801 U | 10/1984 |
| JP | S-61-176357 A | 8/1986 |
| JP | 62144652 A | 6/1987 |
| JP | S-62-144652 U | 6/1987 |
| JP | H-06-510210 A | 11/1994 |
| JP | H06510210 A | 11/1994 |
| JP | H-07-308312 A | 11/1995 |
| JP | H-11-37845 A | 2/1999 |
| JP | 2000-227390 A | 8/2000 |
| JP | 2002-331031 A | 11/2002 |
| JP | 2003-075436 A | 3/2003 |
| JP | 2005-052288 A | 3/2005 |
| JP | 3701031 B2 | 9/2005 |
| JP | 2006-280445 A | 10/2006 |
| JP | 2007-101482 | 4/2007 |
| JP | 2008-055142 A | 3/2008 |
| JP | 2008-519604 A | 6/2008 |
| JP | 2010-516429 A | 5/2010 |
| JP | 2011-036371 A | 2/2011 |
| JP | 2011-515681 A | 5/2011 |
| JP | 2011-252804 A | 12/2011 |
| JP | 2013501937 A | 1/2013 |
| WO | WO-92/17787 A1 | 10/1992 |
| WO | WO-1996/039927 A1 | 12/1996 |
| WO | WO-2006/053208 A1 | 5/2006 |
| WO | WO-2008/094703 A2 | 8/2008 |
| WO | WO-2008094703 A3 | 8/2009 |
| WO | WO-2009/117652 A1 | 9/2009 |
| WO | WO-2011/019576 A1 | 2/2011 |
| WO | WO-2011/145351 A1 | 11/2011 |
| WO | WO-2013/009709 A2 | 1/2013 |
| WO | WO-2013/138356 A2 | 9/2013 |
| WO | WO-2013/172874 A1 | 11/2013 |
| WO | WO-2013/173356 A1 | 11/2013 |
| WO | WO-2013138356 A3 | 12/2013 |
| WO | WO-2014/025415 A2 | 2/2014 |
| WO | WO-2013009709 A3 | 5/2014 |
| WO | WO-2014071399 A1 | 5/2014 |
| WO | WO-2014025415 A3 | 6/2015 |
| WO | WO-2015/160997 A1 | 10/2015 |

OTHER PUBLICATIONS

Adkins, A.R. et al. (2014). "Accuracy of blood loss estimations among anesthesia providers," *AANA Journal* 82(4):300-306.

Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>, 6 pages.

(56) References Cited

OTHER PUBLICATIONS

Al-Kadri, H.M. et al. (2014). "Effect of education and clinical assessment on the accuracy of post partum blood loss estimation," *BMC Preg. Childbirth* 14:110, 7 total pages.
AWHONN Practice Brief (2014). "Quantification of blood loss: AWHONN practice brief No. 1," *AWHONN* p. 1-3.
Bellad, et al. (2009). "Standardized Visual Estimation of Blood Loss during Vaginal Delivery with Its Correlation Hematocrit Changes—A Descriptive Study." South Asian Federation of Obstetrics and Gynecology 1:29-34.
Bose, P. et al. (2006). "Improving the accuracy of estimated blood loss at obstetric haemorrhage using clinical reconstructions," *BJOG* 113(8):919-924.
Corrected Notice of Allowability dated Sep. 15, 2017, for U.S. Appl. No. 14/687,842, filed Apr. 15, 2015, 2 pages.
Eipe, N. et al. (2006). "Perioperative blood loss assessment—How accurate?" *Indian J. Anaesth.* 50(1):35-38.
Extended European Search Report dated Apr. 1, 2015, for EP Application No. 12 810 640.8, filed on Jul. 9, 2012, 8 pages.
Extended European Search Report dated Nov. 23, 2015, for EP Application No. 13 790 688.9, filed on May 14, 2013, 9 pages.
Extended European Search Report dated Nov. 17, 2015, for EP Application No. 13 790 449.6, filed on Jan. 10, 2013, 8 pages.
Extended European Search Report dated Nov. 4, 2016, for EP Application No. 16 183 350.4, filed on Jul. 9, 2012, 9 pages.
Extended European Search Report dated Jul. 26, 2017, for EP Application No. 15 780 653.0, filed on Apr. 15, 2015, 12 pages.
Extended European Search Report dated Jul. 9, 2019, for EP Application No. 16 880 150.4, filed on Dec. 23, 2016, 9 pages.
Extended European Search Report dated Jul. 12, 2019, for EP Application No. 19 156 549.8, filed on Jul. 9, 2012, 8 pages.
Final Office Action dated Feb. 12, 2016, for U.S. Appl. No. 13/544,664, filed Jul. 9, 2012, 9 pages.
Final Office Action dated Aug. 26, 2016, for U.S. Appl. No. 13/894,054, filed May 14, 2013, 7 pages.
Final Office Action dated Jul. 26, 2016, for U.S. Appl. No. 14/876,628, filed Oct. 6, 2015, 5 pages.
Habak, P.J. et al. (2016). "A comparison of visual estimate versus calculated estimate of blood loss at vaginal delivery," *British J. Med. Medical Res.* 11(4):1-7.
Holmes, A.A. et al. (2014). "Clinical evaluation of a novel system for monitoring surgical hemoglobin loss," *Anesth. Analg.* 119(3):588-594.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.
International Search Report dated Mar. 26, 2013, for PCT Application No. PCT/US2013/021075, filed on Jan. 10, 2013, 2 pages.
International Search Report dated Jul. 24, 2015, for PCT Application No. PCT/US2015/026036, filed on Apr. 15, 2015, 2 pages.
International Search Report dated Mar. 30, 2017, for PCT Application No. PCT/US2016/068540, filed on Dec. 23, 2016, 3 pages.
Jones, R. (2015). "Quantitative measurement of blood loss during delivery," *AWHONN* p. S41.
Kamiyoshihara, M. et al. (2008). "The Utility of an Autologous Blood Salvage System in Emergency Thoracotomy for a Hemothorax After Chest Trauma," *Gen. Thorac. Cardiovasc. Surg.* 56:222.
Lyndon, A. et al. (2010). "Blood loss: Clinical techniques for ongoing quantitative measurement," *CMQCC Obstetric Hemorrhage Toolkit*, pp. 1-7.
Lyndon, A. et al. (2015). "Cumulative quantitative assessment of blood loss," *CMQCC Obstetric Hemorrhage Toolkit Version 2.0*, pp. 80-85.
Manikandan, D. et al. (2015). "Measurement of blood loss during adenotonsillectomy in children and factors affecting it," *Case Reports in Clinical Medicine* 4:151-156.
Merck for Mother's Program (2012). Blood loss measurement: Technology opportunity assessment, 9 total pages.
Non-Final Office Action dated Aug. 13, 2015, for U.S. Appl. No. 13/544,664, filed Jul. 9, 2012, 8 pages.
Non-Final Office Action dated Aug. 2, 2016, for U.S. Appl. No. 13/544,664, filed Jul. 9, 2012, 6 pages.
Non-Final Office Action dated May 9, 2014, for U.S. Appl. No. 13/544,679, filed Jul. 9, 2012, 7 pages.
Non-Final Office Action dated Mar. 30, 2016, for U.S. Appl. No. 13/894,054, filed May 14, 2013, 8 pages.
Non-Final Office Action dated Sep. 5, 2014, for U.S. Appl. No. 13/738,919, filed Jan. 10, 2013, 8 pages.
Non-Final Office Action dated Mar. 20, 2015, for U.S. Appl. No. 14/613,807, filed Feb. 4, 2015, 8 pages.
Non-Final Office Action dated Dec. 15, 2015, for U.S. Appl. No. 14/876,628, filed Oct. 6, 2015, 8 pages.
Non-Final Office Action dated Mar. 24, 2017, for U.S. Appl. No. 14/687,842, filed Apr. 15, 2015, 27 pages.
Non-Final Office Action dated Apr. 20, 2017, for U.S. Appl. No. 13/894,054, filed May 14, 2013, 7 pages.
Non-Final Office Action dated Apr. 11, 2018, for U.S. Appl. No. 15/416,986, filed Jan. 26, 2017, 7 pages.
Non-Final Office Action dated Oct. 19, 2018, for U.S. Appl. No. 15/390,017, filed Dec. 23, 2016, 12 pages.
Non-Final Office Action dated Feb. 21, 2019, for U.S. Appl. No. 15/594,017, filed May 12, 2017, 23 pages.
Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Notice of Allowance dated Aug. 3, 2017, for U.S. Appl. No. 14/687,842, filed Apr. 15, 2015, 9 pages.
Notice of Allowance dated Nov. 20, 2017, for U.S. Appl. No. 13/894,054, filed May 14, 2013, 8 pages.
Notice of Allowance dated Jan. 24, 2019, for U.S. Appl. No. 15/416,986, filed Jan. 26, 2017, 9 pages.
Notice of Allowance dated May 3, 2019, for U.S. Appl. No. 15/390,017, filed Dec. 23, 2016, 11 pages.
Pogorelc, D. iPads in the OR: New Mobile Platform to Monitor Blood Loss During Surgery. MedCityNews, Jun. 6, 2012. http://medcitynews.com/2012/06/ipads-in-the-or-new-mobile-platform-to-monitor-blood-loss-during-surgery, 4 pages.
Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.
Sant, et al. "Exsanguinated Blood Volume Estimation Using Fractal Analysis of Digital Images." Journal of Forensic Sciences 57.3 (2012): 610-17.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):S54-S59.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Jul. 24, 2015, for PCT Application No. PCT/US2015/026036, filed on Apr. 15, 2015, 6 pages.

(56) References Cited

OTHER PUBLICATIONS

Written Opinion of the International Searching Authority dated Mar. 30, 2017, for PCT Application No. PCT/US2016/068540, filed on Dec. 23, 2016, 8 pages.
"U.S. Appl. No. 13/738,919, Response filed Oct. 21, 2014 to Non Final Office Action dated Sep. 5, 2014", 8 pgs.
"U.S. Appl. No. 14/072,625, Notice of Allowance dated Feb. 17, 2015", 10 pgs.
"U.S. Appl. No. 14/072,632, Advisory Action dated May 24, 2016", 3 pgs.
"U.S. Appl. No. 14/072,632, Final Office Action dated Feb. 1, 2016", 24 pgs.
"U.S. Appl. No. 14/072,632, Non Final Office Action dated Aug. 4, 2015", 21 pgs.
"U.S. Appl. No. 14/072,632, Notice of Allowance dated Feb. 8, 2017", 9 pgs.
"U.S. Appl. No. 14/072,632, Notice of Allowance dated Jul. 5, 2016", 9 pgs.
"U.S. Appl. No. 14/072,632, Notice of Allowance dated Oct. 19, 2016", 9 pgs.
"U.S. Appl. No. 14/072,632, Response filed May 4, 2016 to Final Office Action dated Feb. 1, 2016", 14 pgs.
"U.S. Appl. No. 14/072,632, Response filed Oct. 28, 2015 to Non Final Office Action dated Aug. 4, 2015", 16 pgs.
"U.S. Appl. No. 14/613,807, Response filed Apr. 24, 2015 to Non Final Office Action dated Mar. 20, 2015", 9 pgs.
"U.S. Appl. No. 14/876,628, 312 Amendment filed Jan. 26, 2017", 3 pgs.
"U.S. Appl. No. 14/876,628, PTO Response to Rule 312 Communication dated Feb. 7, 2017", 2 pgs.
"U.S. Appl. No. 14/876,628, Response filed Apr. 11, 2016 to Non Final Office Action dated Dec. 15, 2015", 11 pgs.
"U.S. Appl. No. 14/876,628, Response filed Sep. 26, 2016 to Final Office Action dated Jul. 26, 2016", 10 pgs.
"U.S. Appl. No. 15/416,986, 312 Amendment filed Feb. 20, 2019", 8 pgs.
"U.S. Appl. No. 15/416,986, Examiner Interview Summary dated Jan. 11, 2019", 2 pgs.
"U.S. Appl. No. 15/416,986, Notice of Allowability dated Apr. 8, 2019", 4 pgs.
"U.S. Appl. No. 15/416,986, Preliminary Amendment filed Jan. 26, 2017", 3 pgs.
"U.S. Appl. No. 15/416,986, Preliminary Amendment filed Aug. 28, 2017", 6 pgs.
"U.S. Appl. No. 15/416,986, Response filed Oct. 11, 2018 to Non Final Office Action dated Apr. 11, 2018", 13 pgs.
"Chinese Application Serial No. 201380037022.9, Office Action dated Mar. 28, 2017", with English translation of claims, 28 pgs.
"Chinese Application Serial No. 201380037022.9, Office Action dated Jul. 10, 2018", with English translation of claims, 8 pgs.
"Chinese Application Serial No. 201380037022.9, Office Action dated Dec. 4, 2017", with English translation of claims, 32 pgs.
"Chinese Application Serial No. 201910039633.6, Office Action dated Nov. 15, 2019", w/o English Translation, 12 pgs.
"European Application Serial No. 13790449.6, Communication Pursuant to Article 94(3) EPC dated Apr. 9, 2019", 5 pgs.
"European Application Serial No. 13790449.6, Communication Pursuant to Article 94(3) EPC dated Feb. 14, 2018", 7 pgs.
"European Application Serial No. 13790449.6, Response filed Jun. 6, 2016 to Extended European Search Report dated Nov. 17, 2015", 12 pgs.
"European Application Serial No. 13790449.6, Response filed Jun. 18, 2015 to Communication pursuant to Rules 161 (2) and 162 EPC dated Dec. 23, 2014", 10 pgs.
"European Application Serial No. 13790449.6, Response filed Jun. 25, 2018 to Communication Pursuant to Article 94(3) EPC dated Feb. 14, 2018", 7 pgs.
"European Application Serial No. 13790449.6, Response filed Aug. 19, 2019 to Communication Pursuant to Article 94(3) EPC dated Apr. 9, 2019", 10 pgs.
"International Application Serial No. PCT/US2013/021075, International Preliminary Report on Patentability dated Nov. 27, 2014", 8 pgs.
"International Application Serial No. PCT/US2013/068576, International Preliminary Report on Patentability dated May 14, 2015", 8 pgs.
"International Application Serial No. PCT/US2013/068576, International Search Report dated Apr. 4, 2014", 5 pgs.
"International Application Serial No. PCT/US2013/068576, Invitation to Pay Additional Fees dated Jan. 23, 2014", 2 pgs.
"International Application Serial No. PCT/US2013/068576, Written Opinion dated Apr. 4, 2014", 6 pgs.
"International Application Serial No. PCT/US2016/032560, International Search Report dated Aug. 19, 2016", 2 pgs.
"International Application Serial No. PCT/US2016/032560, Written Opinion dated Aug. 19, 2016", 6 pgs.
"Japanese Application Serial No. 2015-512621, Office Action dated Jan. 12, 2016", with English translation of claims, 8 pgs.
"Japanese Application Serial No. 2015-512621, Office Action dated Aug. 23, 2016", with English translation of claims, 6 pgs.
"Japanese Application Serial No. 2015-512621, Response filed Apr. 11, 2016 to Office Action dated Jan. 12, 2016", with English translation of claims, 7 pgs.
"Japanese Application Serial No. 2016-246268, Office Action dated Oct. 31, 2017", with English translation of claims, 6 pgs.
"Japanese Application Serial No. 2016-246268, Response filed Apr. 25, 2018 to Office Action dated Oct. 31, 2017", with English translation of claims, 6 pgs.
Kamiyoshihara, M, et al., "The Utility of an Autologous Blood Salvage System in Emergency Thoracotomy for a Hemothorax After Chest Trauma", Gen. Thorac. Cargiovasc. Surg. vol. 56, (2008), 222.
Satish, S, et al., "Method for Projecting Blood Loss of a Patient During a Surgery", U.S. Appl. No. 15/154,921, filed May 13, 2016, 50 pgs.
Satish, S, et al., "System and Methods for Managing Blood Loss of a Patient", U.S. Appl. No. 15/943,561, filed Apr. 2, 2018, 66 pgs.
U.S. Appl. No. 13/738,919, U.S. Pat. No. 8,983,167, filed Jan. 10, 2013, System and Method for Estimating a Quantity of a Blood Component in a Fluid Canister.
U.S. Appl. No. 14/613,807, U.S. Pat. No. 9,171,368, filed Feb. 4, 2015, System and Method for Estimating a Quantity of a Blood Component in a Fluid Canister.
U.S. Appl. No. 14/876,628, U.S. Pat. No. 9,595,104, filed Oct. 6, 2015, System and Method for Estimating a Quantity of a Blood Component in a Fluid Canister.
U.S. Appl. No. 15/416,986, U.S. Pat. No. 10,282,839, filed Jan. 26, 2017, System and Method for Estimating a Quantity of a Blood Component in a Fluid Canister.
U.S. Appl. No. 14/072,625, U.S. Pat. No. 9,047,663, filed Nov. 5, 2013, Method for Triggering Blood Salvage.
U.S. Appl. No. 14/072,632, U.S. Pat. No. 9,646,375, filed Nov. 5, 2013, Method for Setting a Blood Transfusion Parameter.

\* cited by examiner

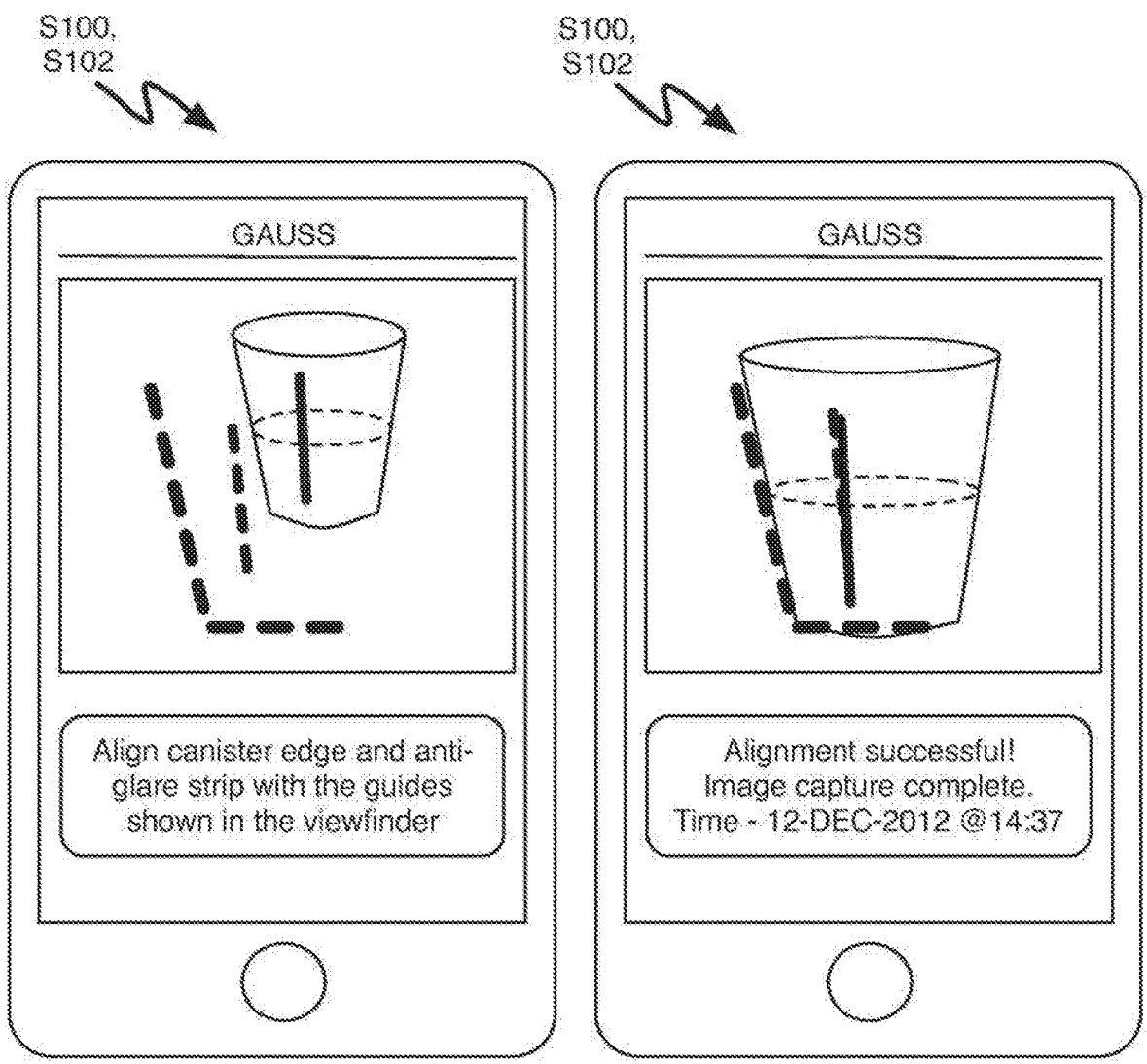

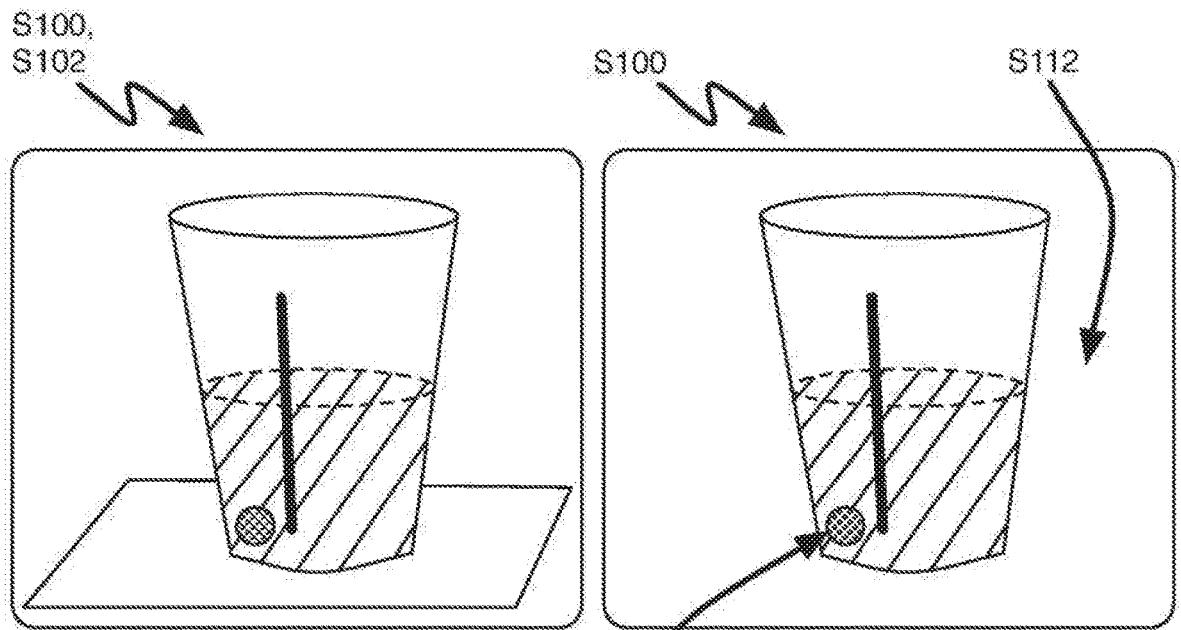
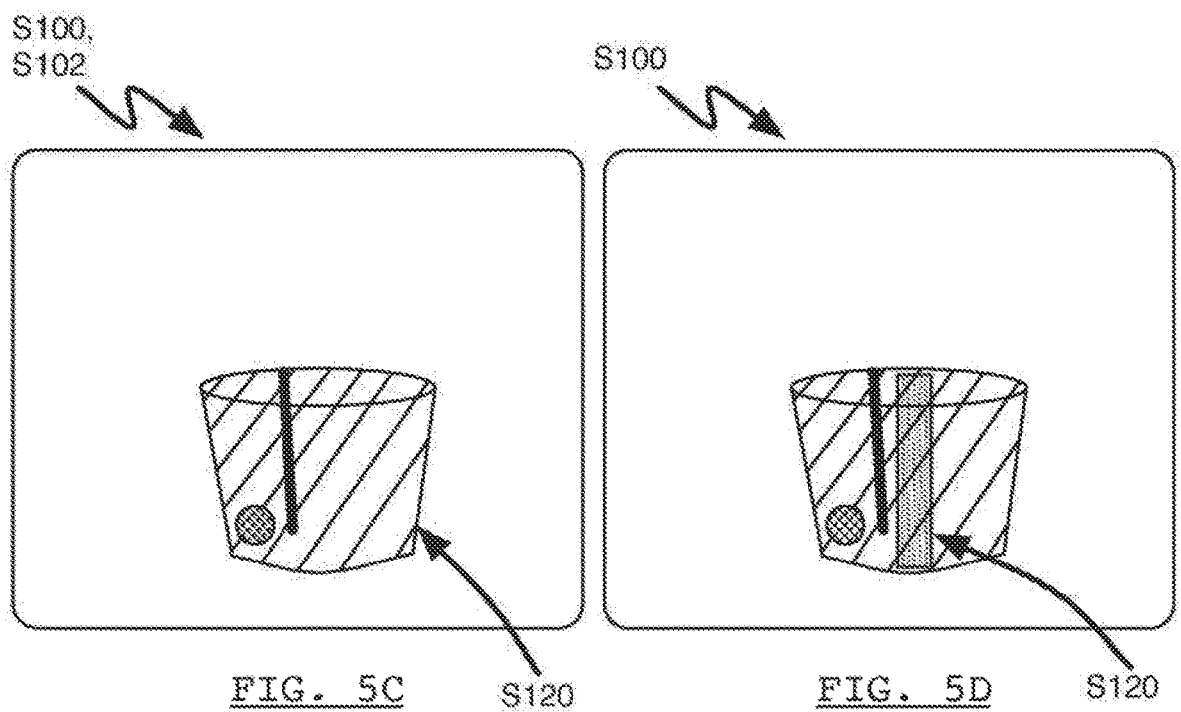

SYSTEM AND METHOD FOR ESTIMATING A QUANTITY OF A BLOOD COMPONENT IN A FLUID CANISTER

CROSS-REFERENCE TO RELATED APPLICATIONS

This application is a continuation of U.S. patent application Ser. No. 15/416,986, filed Jan. 26, 2017, which is a continuation of U.S. patent application Ser. No. 14/876,628 (now U.S. Pat. No. 9,595,104), filed Oct. 6, 2015, which is a continuation of U.S. patent application Ser. No. 14/613,807 (now U.S. Pat. No. 9,171,368), filed Feb. 4, 2015, which is a continuation of U.S. patent application Ser. No. 13/738,919 (now U.S. Pat. No. 8,983,167), filed Jan. 10, 2013, which claims the benefit of U.S. Provisional Patent Application No. 61/703,179, filed on Sep. 19, 2012, U.S. Provisional Patent Application No. 61/646,822, filed May 14, 2012, and U.S. Provisional Patent Application No. 61/722,780, filed on Nov. 5, 2012, all of which are incorporated in their entireties by this reference.

This application is related to U.S. patent application Ser. No. 13/544,646, filed on 9 Jul. 2012, which is incorporated in its entirety by this reference.

TECHNICAL FIELD

This invention relates generally to the surgical field, and more specifically to a new and useful system and method for estimating the extracorporeal blood volume in a canister for use in surgical practice.

BACKGROUND

Overestimation and underestimation of patient blood loss is a significant contributor to high operating and surgical costs for hospitals, clinics and other medical facilities. Specifically, overestimation of patient blood loss results in wasted transfusion-grade blood and higher operating costs for medical institutions and can lead to blood shortages. Underestimation of patient blood loss is a key contributor of delayed resuscitation and transfusion in the event of hemorrhage and has been associated with billions of dollars in avoidable patient infections, re-hospitalizations, and lawsuits annually.

Thus, there is a need in the surgical field for a new and useful method for estimating a quantity of a blood component in a fluid canister. This invention provides such a new and useful system and method.

BRIEF DESCRIPTION OF THE FIGURES

FIGS. 4A and 4B are graphical representations in accordance with one variation of the method;

FIGS. 5A, 5B, 5C, and 5D are graphical representations in accordance with variations of the method;

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Methods

Figure 1:
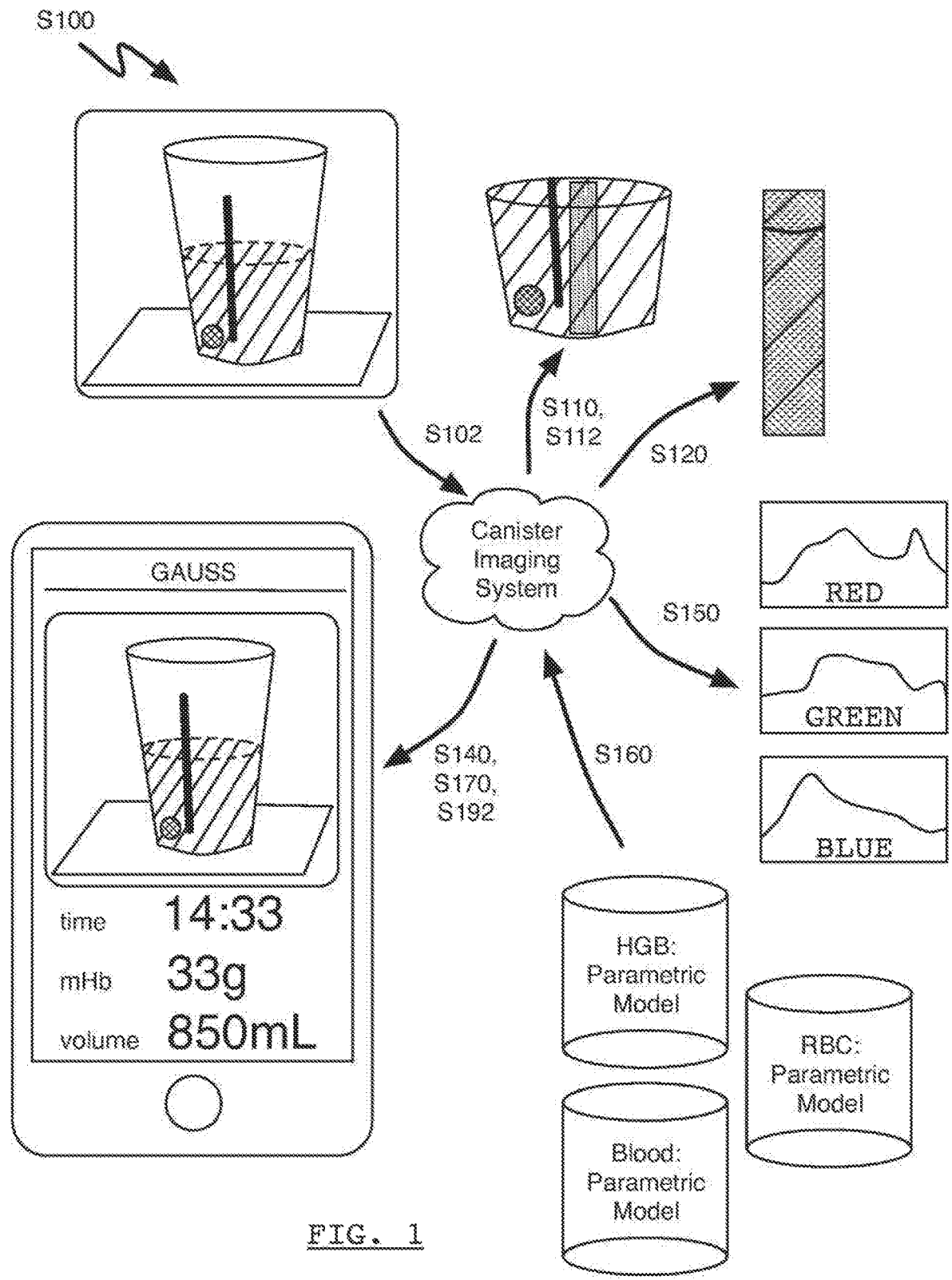
FIG. 1 is a flowchart representation of a method of one embodiment.
Figure 2:
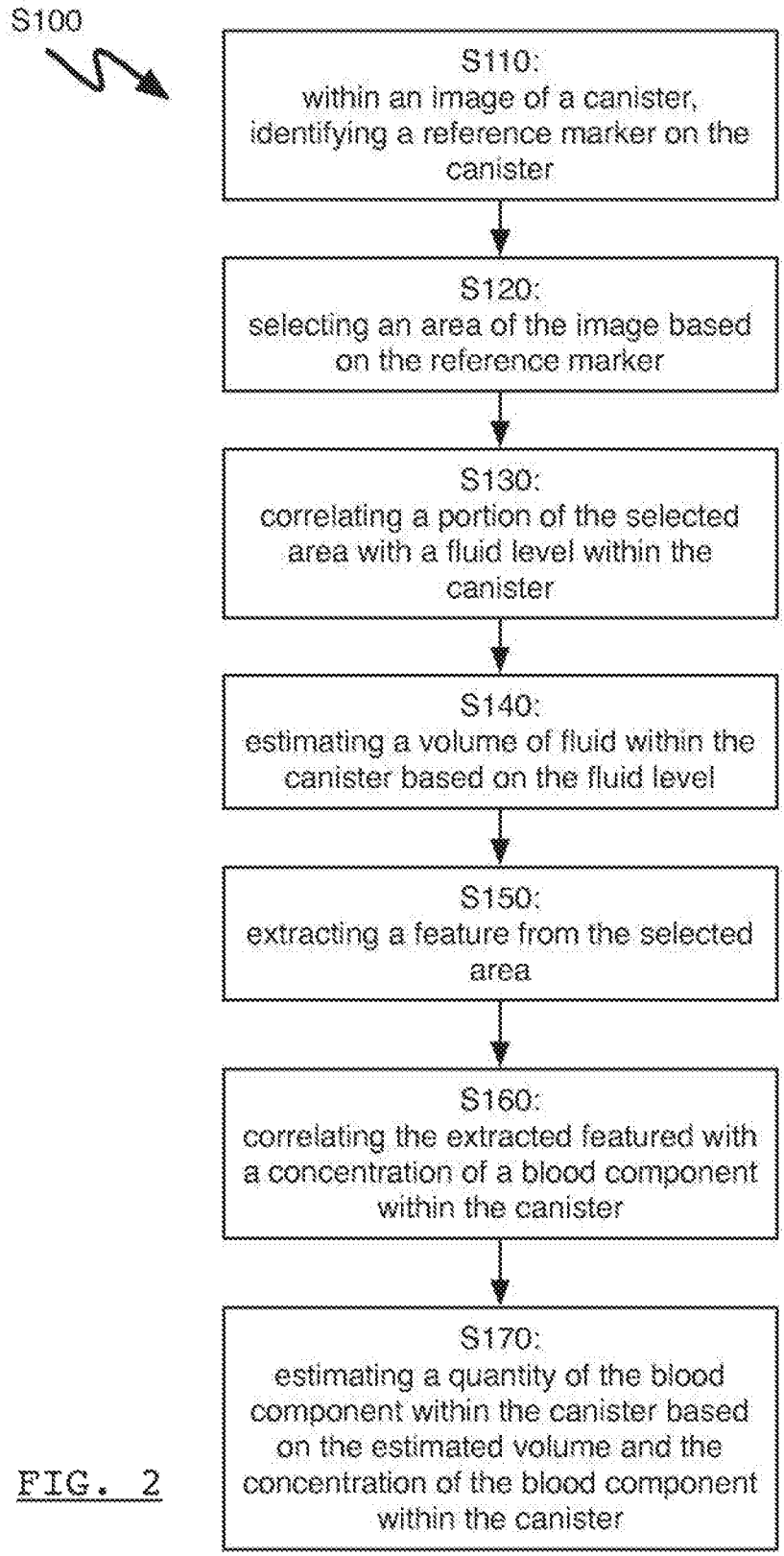
FIG. 2 is a flowchart representation of one variation of the method.

As shown in FIGS. 1 and 2, a method S100 for estimating a quantity of a blood component in a fluid canister includes: within an image of a canister, identifying a reference marker on the canister in Block S110; selecting an area of the image based on the reference marker in Block S120; correlating a portion of the selected area with a fluid level within the canister in Block S130; estimating a volume of fluid within the canister based on the fluid level in Block S140; extracting a feature from the selected area in Block S150; correlating the extracted featured with a concentration of a blood component within the canister in Block S160; and estimating a quantity of the blood component within the canister based on the estimated volume and the concentration of the blood component within the canister in Block S170.

Figure 3:
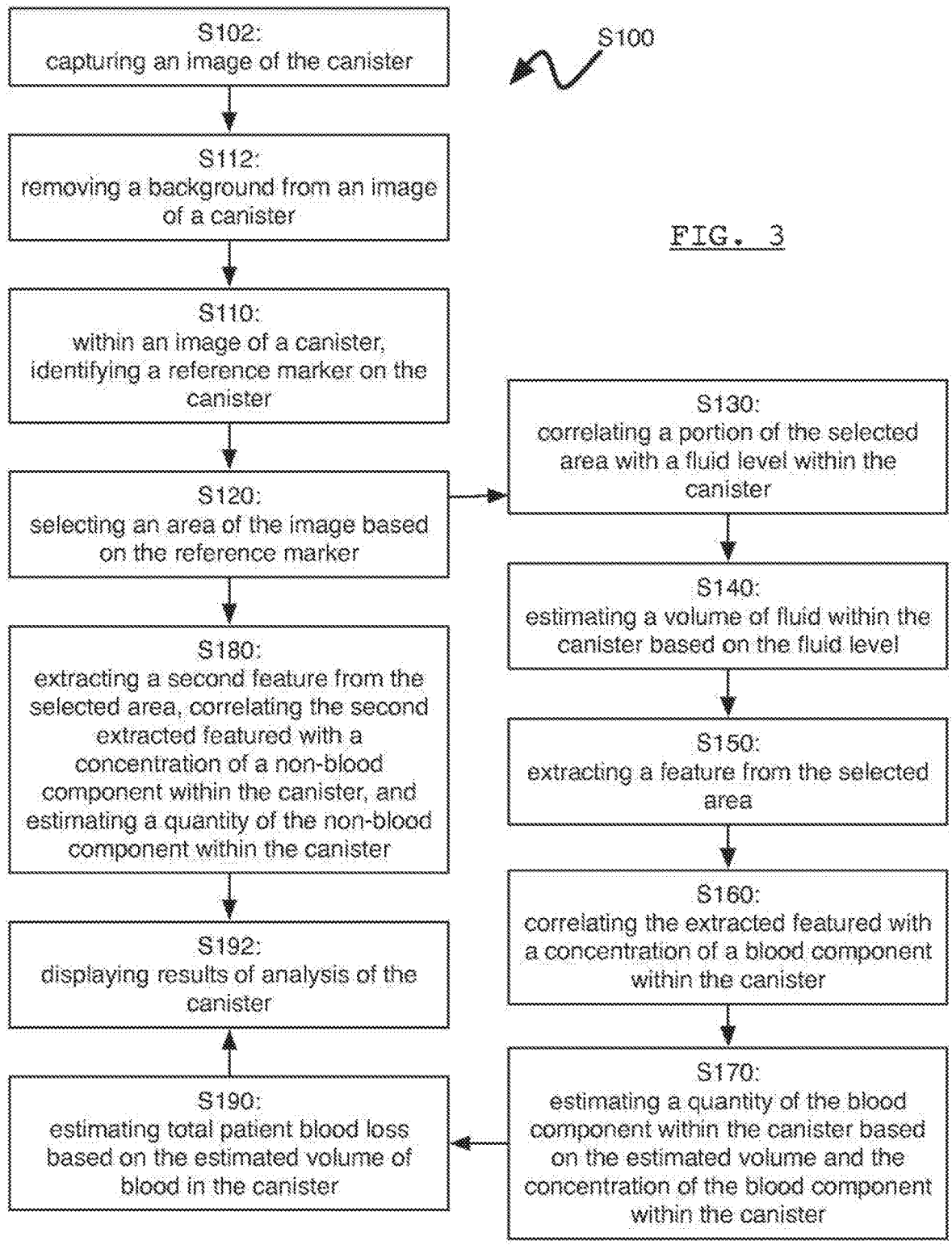
FIG. 3 is a flowchart representation of one variation of the method.

As shown in FIG. 3, one variation of the method S100 includes: removing a background from an image of a canister in Block S112; correlating a segment of the image with a portion of the canister containing fluid in Block S120; estimating a volume of fluid within the canister based on the segment in Block S140; extracting a color feature from a pixel within the segment in Block S150; correlating the color feature with a concentration of a blood component within the canister in Block S160; and estimating a content of the blood component within the canister based on the estimated volume of fluid and the concentration of the blood component within the fluid canister in Block 170.

The method S100 functions to implement machine vision to estimate the content of a blood component within a fluid canister. Generally, the method S100 can analyze an image of a fluid canister to determine a fluid volume within the canister in Block S140 and a concentration of the blood component in Block S160, data that can be combined to derive the content of the blood component within the canister in Block S170. The method S100 can therefore recite a variation of and/or implement techniques described in U.S. patent application Ser. No. 13/544,646, which is incorporated herein by reference.

The blood component can be any of whole blood, red blood cells, hemoglobin, platelets, plasma, or white blood cells. However, the method S100 can also implement Block S180, which recites estimating a quantity of a non-blood component within the canister based on the estimated volume and the concentration of the non-blood component within the canister. The non-blood component can be saline, ascites, bile, irrigant saliva, gastric fluid, mucus, pleural fluid, urine, fecal matter, or any other bodily fluid of a patient.

The fluid canister can be a suction canister implemented in a surgical or other medical, clinical, or hospital setting to collect blood and other bodily fluids, wherein the fluid canister can be translucent or substantially transparent such that the method S100 can identify and analyze fluid contained within the canister. The canister can alternatively be a blood salvage canister, an intravenous fluid bag, or any other suitable blood- or fluid-bearing container for collecting surgical waste or recovering biological fluid. For example, the canister can be a surgical fluid canister including: a translucent container configured to hold a fluid, the container including a wall and a series of horizontal fluid volume indicator markings arranged along the wall and visible from external the container; and an anti-glare strip arranged on an external surface of the wall. The anti-glare strip can be arranged on the container such that the area selected from an image of the canister in Block S120 of the method S100 includes at least a portion of the anti-glare strip. The anti-glare strip can therefore be positioned on the container to reduce glare on the portion of the container corresponding to the selected area of the image, thus reducing glare-induced errors in the estimated content of the blood component in the canister. The anti-glare strip can be an adhesive strip, such as Scotch tape by 3M or a marking printed on an external surface of the surgical fluid canister, and the anti-glare strip can include a dull, matte, satin, or other suitable anti-glare surface finish. The anti-glare strip can also be a narrow strip extending from proximal the bottom of the surgical fluid canister to proximal the top of the surgical fluid canister, though the anti-glare strip can be of any other form, geometry, material, or surface finish and can be applied to the surgical fluid canister in any other way. However, the fluid canister can be any other suitable type of canister including any other suitable feature.

Because any of the foregoing blood and non-blood fluids can be collected in the fluid canister in any quantity and concentration during a surgery or other medical event, and because fluid content and concentration cannot be estimated substantially in real time through canister volume readings alone, the method S100 can be useful in quantifying an amount and/or concentration of a blood component (e.g., hemoglobin) and/or other fluids (e.g., saline). Furthermore, from this derived data, the volume of extracorporeal blood in the fluid canister can be estimated, thus enabling substantially comprehensive blood loss monitoring, particularly when implemented alongside any of the method S100s described in U.S. patent application Ser. No. 13/544,646, which is incorporated herein by reference, which describes estimating extracorporeal blood volume in surgical sponges, in surgical towels, and/or on other surfaces.

The method S100 is can be implemented by a computer system as a fluid canister analyzer that analyzes a photographic image to estimate the content of a fluid canister. The computer system can be cloud-based (e.g., Amazon EC2 or EC3), a mainframe computer system, a grid-computer system, or any other suitable computer system. The method S100 can therefore be implemented by a handheld (e.g., mobile) computing device, such by a smartphone, digital music player, or tablet computer executing a native blood component analysis application as shown in FIGS. 1 and 4A. For example, a camera integral with the computing device can capture the image of the fluid canister, and a processor integral with the computing device implement Blocks S110, S120, S130, etc. Additionally or alternatively, the computing device can communicate with a remote server, such as over the Internet via a wireless connection, wherein the server performs at least some Blocks of the method S100 and wherein at least some of the outputs of the method S100 are transmitted back to the computing device for further analysis and/or subsequent release to a user. The computing device can also include or be coupled to a digital display such that the method S100 can display information to a user (e.g., a nurse or anesthesiologist) through the display.

Alternatively, the method S100 can be implemented as a standalone blood volume estimation system including a fluid canister, a fluid canister stand, a camera, a camera stand configured to support the camera adjacent the fluid canister, a digital display, a processor configured to perform at least a portion of the method S100, and/or a communication module configured to communicate with a remote server that performs at least a portion of the method S100. In this implementation, the camera can be substantially non-transiently positioned relative to a fluid canister stand such that the camera remains in a suitable position to capture an image of a canister substantially throughout a surgery or other medical event and/or until the canister is full. This can enable the camera to regularly capture and analyze images of the fluid canister, such as every thirty seconds or every two minutes. This system implementing the method S100 can further communicate (e.g., via Bluetooth) with another one or more systems implementing any one or more of methods of U.S. patent application Ser. No. 13/544,646 to enable a substantially comprehensive estimate of extracorporeal blood volume and thus total patient blood loss. However, the method S100 can be implemented in or by any other computer system, computing device, or combination thereof.

As shown in FIG. 3, one variation of the method S100 includes Block S102, which recites capturing an image of the canister. Block S102 can interface with a camera or other suitable optical sensor to capture the image of a field of view of the camera or optical sensor, wherein the canister is in the field of view of the camera or optical sensor. As shown in FIG. 5A, Block S102 can capture the image that is a static, single-frame image including at least a portion of the fluid canister. Alternatively, Block S102 can capture the image that is a multi-frame video feed including multiple static images of the fluid canister. The image can be a color image, a black and white image, a grayscale image, an infrared image, a field of view of an optical sensor, a fingerprint of a field of view of an optical sensor, a point cloud, or any other suitable type of image.

Figures 7A, 7B:
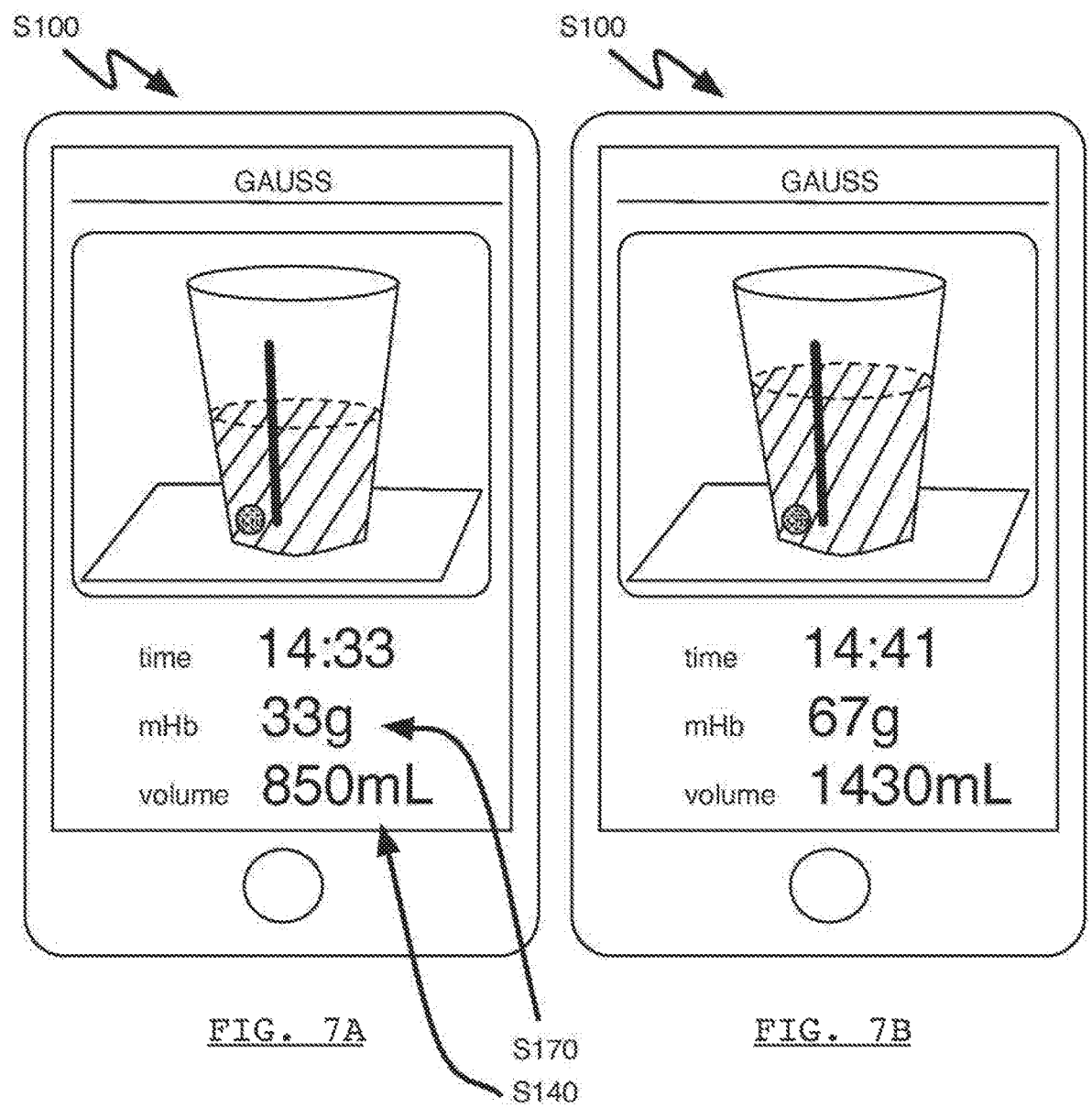
FIGS. 7A and 7B are graphical representations in accordance with one variation of the method.

In one implementation, Block S102 captures the image of the canister according to a time schedule, such as every thirty seconds or every two minutes during a surgery. Alternatively, Block S102 can implement machine vision and/or machine recognition techniques to identify the canister within the field of view of the optical sensor and trigger image capture once a canister (or other blood-containing item) is detected. For example, Block S102 can capture an image of the field of view of the canister each time a user holds the camera (e.g., the computing device that incorporates the camera) up to the fluid canister. Similarly, Block S102 can cooperate with Block S140 to capture the image of the canister once a threshold increase is canister fluid volume is detected. Therefore, Block S112 can capture images of the canister automatically, such as based on a timer, changes in canister fluid volume, or availability of the canister for imaging, which can enable the method S100 to track fluid collection in the canister over time, as shown in FIGS. 7A and 7B. This can be useful in mapping trends in patient fluid loss and/or predicting future patient fluid (e.g., blood) loss. Alternatively, Block S102 can capture the image of the canister according to a manual input, such as from a nurse or anesthesiologist.

In the foregoing implementations, Block S102 can further guide a user in capturing the image of the fluid canister. For example, as shown in FIGS. 4A and 4B, Block S102 can display an alignment graphic on a display of the computing device, wherein the display also functions as a viewfinder for a camera incorporated into the computing device. In this example, Block S102 can prompt the user to align an edge of the canister in the field of view of the camera with the alignment graphic rendered on the display, as shown in FIG. 4A. The alignment graphic can include points, lines, and/or shapes (e.g., an outline of a canister) to be aligned with a side, feature, decal, and/or the reference marker of or on the fluid canister. Block S102 can thus guide a user in properly positioning the canister relative the camera (or other optical sensor) in preparation for imaging. The alignment graphics can additionally or alternatively include curves suggestive of a perspective view of the fluid canister, which can guide the user in positioning the canister in a preferred orientation, (e.g., vertical and/or horizontal pitch) relative to and/or distance from the camera. Block S102 can also interface with a light source or flash system to control lighting of the canister during image capture of the canister. Block S102 can additionally or alternatively alert a user, such as with an audible or visual alarm, if lighting of the canister was insufficient or too poor to enable substantially accurate estimation of fluid volume of blood content of the canister. Block S102 can thus enable image capture of the fluid canister with a substantially high degree of accuracy and repeatability with predictable canister positioning, lighting compensation, etc., which can further enable substantially accurate and repeatable blood component content estimations in Block S170.

Block S102 can also timestamp each image of the canister as the canister is filled, replaced, and/or emptied, which can further enable the method S100 to track changes in fluid level within the canister, map patient blood (and fluid) loss trends, etc. However, Block S102 can function in any other way to capture the image of the canister.

Block S110 of the method S100 recites, within an image of a canister, identifying a reference marker on the canister. Generally, Block S110 functions recognize a canister-related marker within the image. By identifying the marker, Block S110 can enable analysis of particular portions of the image in subsequent Blocks. Block S110 can implement any suitable machine vision technique and/or machine learning technique to identify the reference marker. For example, Block S120 can implement object localization, segmentation (e.g. edge detection, background subtraction, grab-cut-based algorithms, etc.), gauging, clustering, pattern recognition, template matching, feature extraction, descriptor extraction (e.g. extraction of texton maps, color histograms, HOG, SIFT, MSER (maximally stable extremal regions for removing blob-features from the selected area) etc.), feature dimensionality reduction (e.g. PCA, K-Means, linear discriminant analysis, etc.), feature selection, thresholding, positioning, color analysis, parametric regression, non-parametric regression, unsupervised or semi-supervised parametric or non-parametric regression, or any other type of machine learning or machine vision to estimate a physical dimension of the canister. Block S110 can further compensate for varying lighting conditions of the canister, variations in fluid compositions canister (e.g., widely varying color, transparency, refractive indices, etc.), lens- or software-based optical distortion in the image, or any other inconsistency or variable prevalent in any use scenario.

In one implementation, Block S110 identifies the reference marker that is a boundary between the canister and a background, which can enable Block S110 to remove a portion of the image corresponding to the background. In another implementation, Block S110 identifies the reference marker that is a symbol arranged on the canister, as shown in FIG. 5B. For example, the symbol can be a manufacturer's label printed on the canister, a fluid volume scale printed on the canister, a colored dot (e.g., sticker) adhered to the outside of the canister, a common (e.g., standardized) marking printed on surgical canisters from a variety of manufacturer's, or any other suitable reference marker. In a further implementation, Block S110 identifies the marker based on surface finish on the canister. For example, Block S110 can identify the marker that is a portion of the canister than includes a matte or other substantially glare-free finish.

Block S110 can additionally or alternatively implement machine vision techniques to identity the type of fluid canister. For example, Block S110 can implement template matching to determine the type of the canister, such as by accessing a template library of reference markers, each reference marker associated with a particular type of canister, such as from a particular manufacturer, of a particular size, and/or of a particular shape. In this implementation, or more subsequent Blocks of the method S100 can be tailored for a specific type of fluid canister, wherein Block S110 functions to set a particular implementation path for the subsequent Blocks dependent on the particular canister type. However, Block S110 can function in any other way to identify any other suitable reference marker in the image of the canister and/or the type of canister.

Block S112 of the method S100 recites removing a background from an image of a canister. Because the background is unlikely to contain useful information related to the volume and/or quality of fluid within the fluid canister, Block S112 excludes substantially unnecessary portions of the image, thus enabling subsequent Blocks of the method S100 to focus analysis on portions of the image (more likely) containing information pertinent to the quality and quantity of fluid in the canister, as shown in FIGS. 5B and 5C. In one implementation, Block S112 applies machine vision, such as edge detection, grab-cut, foreground detection, or any other suitable technique, to isolate a portion of the image associated with the physical canister and to discard the remainder of the image falling outside of a detected boundary of the canister.

In another implementation, Block S112 uses the identified reference marker to anchor a predefined canister perimeter to the image. Block S112 can then discard an area of the image that falls outside of the predefined canister perimeter. For example, Block S112 can select a particular predefined, canister-shaped boundary according to the size and/or geometry of the canister identified in the image in Block S10. Alternatively, Block S112 can receive an input from a user identifying the type of fluid canister and subsequently apply a predefined boundary filter according to the entered canister type. However, Block S112 can function in any other way to remove a background portion from the image of the fluid canister.

Block S120 of the method S100 recites selecting an area of the image based on the reference marker, as shown in FIG. 5D. Generally, Block S120 functions to select a particular area of the image corresponding to a particular region of interest of the surface of the canister. The region of interest can be particularly characteristic of the contents of the canister, such as a region of substantially low glare (e.g., including a matte coating or anti-glare sticker or tape), a region substantially nearest a viewing plane of the camera, a region substantially centered between perceived sides of the canister, and/or a region of the canister substantially free of additional markings, labels, etc. The selected area can further bisect a surface of the fluid within the canister such that Block S130 can subsequently identify the level of fluid within the canister based on analysis of the selection area.

The selected area can therefore be one or more contiguous and/or discontiguous pixels within the image and containing information substantially characteristic of the contents of the canister. Furthermore, the selected are can correspond to a surface of the canister (e.g. a vertical white stripe) that is opaque enough to eliminate background noise but exhibits a substantially abrupt color transition proximal a fluid surface, thus enabling Block S130 to estimate the fluid height in the canister.

In one example implementation, as shown in FIGS. 5C and 5, Block S110 implements machine vision to identify the reference marker arranged at a standardized position on the canister, and Block S120 selects the area of the image according to a standardized distance between the reference marker and the region of interest on the canister, wherein the selected area of the image corresponding to the region of interest on the canister. For example, Block S120 can select the area of the image that is twenty pixels wide and one hundred pixels tall with geometric center offset from the reference marker (e.g., from a determined center pixel of the reference marker) by fifty pixels along the +x axis and seventy pixels along the +y axis of the image.

In another example implementation, Block S110 identifies the reference marker that is a volume marker on the canister, and Block S120 selects the area of the image that is a set of pixels adjacent a portion of the image corresponding to the volume marker. In this example implementation, Block S130 can identify a fluid meniscus within the set of pixels and compare the fluid meniscus to the volume marker in order to estimate the fluid level in the canister. For example, Block S120 can select a rectangular area of the image that is twenty pixels wide and one hundred pixels tall with upper right corner of the area offset from a left edge of the volume marker by ten pixels along the −x axis and twenty pixels along the +y axis of the image.

In yet another example implementation, Block S110 identifies horizontal volume indicator markings on the fluid canister, and Block S120 defines a first horizontal endpoint of the selected area in alignment with a common horizontal endpoint of the volume indicator markings. Block S120 further defines a second horizontal endpoint of the selected area as a median horizontal coordinate of pixels associated with the horizontal volume indicator markings, a first vertical endpoint of the selected area as the bottom boundary of the fluid-containing portion of the fluid canister, and a second vertical endpoint of the selected area on the identified surface of the fluid in the fluid canister. From these four endpoints, Block S120 can select and anchor a rectilinear area of the image. This selected area can thus capture image color information along the full vertical height of fluid in the fluid canister and substantially horizontally centered within the isolated image of the fluid-containing portion of the fluid canister.

In a further example implementation, Block S120 can define the selected area that overlaps substantially completely with the reference marker identified in Block S110. For example, Block S110 can identify the reference marker that is an anti-glare surface (e.g., anti-glare tape) on the canister, and Block S120 can define the selected area that overlaps substantially completely with the reference marker.

Block S120 can similarly recite correlating a segment of the image with a portion of the canister containing fluid, as shown in FIG. 5D. For example, Block S120 can identify a perimeter of the canister within the image and cooperate with Block 130 to identify a surface of the fluid within the canister. Block S130 can then select a segment (i.e. area of the image) of the image bounded by the perimeter of the canister and the surface of the fluid, the segment thus correlated with a portion of the canister that contains fluid. Alternatively, Block S120 can characterize the color of various pixels within a portion of the image correlated with the canister and select the segment that contains pixels characterized as substantially red (e.g., containing blood). However, Block S120 can function in any other way to select an area of the image based on the reference marker and/or correlate a segment of the image with a portion of the canister containing fluid.

Figure 6A:
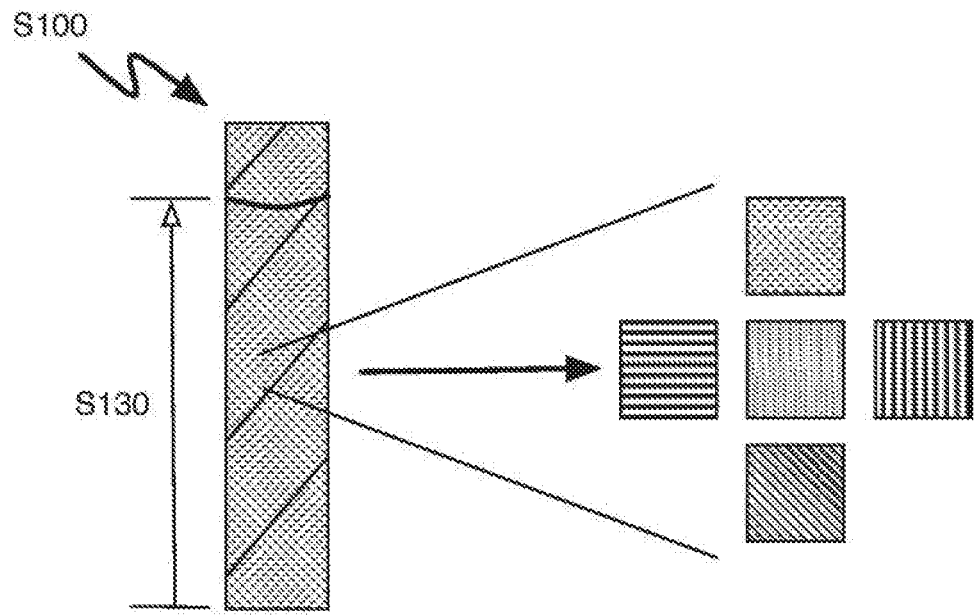
FIGS. 6A and 6B are graphical representations in accordance with one variation of the method.

Block S130 of the method S100 recites correlating a portion of the selected area with a fluid level within the canister. Generally, Bock S130 functions to identify a surface of fluid in the canister and a base of the canister (e.g., a lowest extent of fluid in the canister) and, from this data, estimate a level of fluid within the canister, as shown in FIG. 6A. As described above, the selected area can bisect the surface of the fluid, and Block S130 can therefore analyze the selected area to identify the surface of the fluid. In one example implementation, Block S120 can fit a parametric function (e.g. sigmoid) to an intensity profile of the selected area that corresponds to an anti-glare strip on the canister estimate a fluid height therein. In another example implementation, Block S130 can correlate pixels in the selected area with fluid (e.g. pixels that are substantially red) and calculate an upper bound and a lower bound of fluid in the canister based on the distribution of y-coordinates of the correlated pixels. In this example, Block S130 can define the upper bound as the $95^{th}$ percentile of the y-coordinates, or Block S130 can begin with the $99^{th}$ percentile of the y-coordinates of the correlated pixels and decrement the percentile until the redness of two adjacent pixels does not change beyond a predetermined threshold, though Block S130 can function in any other way to identify and/or ignore "false-positive" 'red' pixels that do not correspond to fluid in the canister.

In one example implementation, Block S130 characterizes the color of each pixel (e.g., a redness value of each pixel) along a vertical line of pixels within the selected area. By scanning the line of pixels from the bottom of the line of pixels (i.e. from proximal the base of the canister) upward, Block S130 can identify a first abrupt shift in pixel color, which can be correlated with a lower bound of the surface of the fluid. By further scanning the line of pixels from the top of the line of pixels (i.e. from proximal the top of the canister) downward, Block S130 can identify a second abrupt shift in pixel color, which can be correlated with an upper bound of the surface of the fluid. Block S130 can average the upper and lower bounds of the surface of the fluid to estimate the level of the fluid within the canister. Alternatively, Block S130 can focus additional analysis on an abbreviated line of pixels between the upper and lower bounds, such as by scanning up and/or down the abbreviated line of pixels to identify more subtle changes in the color of pixels along the line. For example, Block S130 can correlate a subtle lightening of pixel color of higher pixels with a fluid meniscus. In another example, Block S130 can improve the resolution of the estimated surface of the fluid by reanalyzing pixels within subsequent abbreviated pixel lines.

Block S130 can similarly analyze two or more adjacent lines of pixels within the selected area and compare (e.g., average) results of each pixel line analysis to improve accuracy of an estimate of the location of the fluid surface. For example, Block S130 can compare the location of one border pixel in each of a set of pixel lines in the selected area to extract a curved border between a fluid-filled portion of the canister and an empty portion of the canister, and Block S130 can correlate this curved border with a fluid meniscus. Alternatively, Block S130 can estimate the fluid meniscus. For example, Block S130 can implement a lookup table of meniscus sizes and geometries, wherein the lookup table accounts for a type of canister, a fluid characteristic (e.g., redness value correlated with blood and water content in the canister), an angle between the camera and the canister, a distance between the camera and the canister, the level of fluid in the canister that is conical, and/or any other suitable variable.

Block S130 can additionally or alternatively analyze clusters of pixels, such as four-pixel by four-pixel clusters in a four-pixel-wide line of pixels within the pixel area. Block S130 can analyze discrete cluster or pixels or overlapping clusters or pixels, and Block S130 can average a characteristic, such as a redness value or color property, of the pixels in each cluster, such as to reduce error. However, Block S130 can function in any other way to identify the surface of the fluid in the canister.

Block S130 can determine a lower bound of the fluid in the canister by implementing similar methods of comparing pixel characteristics. Alternatively, Block can estimate the lower bound of the fluid to be at or proximal the determined lower boundary of the canister. However, Block S130 can function in any other way to identify the lower bound of the fluid in the canister.

Once Block S130 identifies both the upper and lower bounds of the fluid within the canister, Block S130 can calculate a pixel-based height of the fluid within the fluid canister, such as by counting the number of pixels between the lower and upper bounds at approximately the center of the portion of the image correlated with the canister. Block S130 can subsequently convert the pixel-based distance measurement to a physical distance measurement (e.g., inches, millimeters), such as by translating the pixel value according to the type of canister and/or an actual or estimated angle between the camera and the canister, distance between the camera and the canister, geometry of the canister (e.g., diameters at the canister base and at the fluid surface), and/or any other relevant metric of or between the canister and the camera. Alternately, Block S140 can directly convert the pixel-based fluid level measurement into an estimate fluid volume within the canister.

Block S120 can additionally or alternatively receive a manual input that selects or identifies the reference marker, and Block S130 can similarly additionally or alternatively receive a manual input that selects or identifies the surface of fluid or the height of fluid in the canister. For example, the method S100 can implement manual checks to teach or correct automatic selection of the reference marker and/or estimation of the canister fluid level. Block S120 and Block S130 can thus implement supervised or semi-supervised machine learning to improve selection of the reference marker and/or estimation of the canister fluid level with subsequent samples (i.e. images of one or more canisters). However, Block S120 and Block S130 can function in any other way to select the reference marker and/or estimate the canister fluid level, respectively.

Block S140 of the method 8100 recites estimating a volume of fluid within the canister based on the fluid level. Generally, Block S140 functions to convert the fluid level estimate of Block S130 into a fluid volume estimate based on a canister type and/or geometry, as shown in FIGS. 1 and 7A. For example, the canister can be one of various types of frustoconical fluid canisters of various geometries (e.g., base diameter, sidewall angle, maximum fluid level) used in operating rooms and/or clinical settings to collect bodily fluids of patients. Therefore, once the type and/or geometry of the canister is entered by a user, determined through machine vision techniques, and/or accessed from a canister type and/or geometry database, Block S140 can transform the fluid level estimate into a fluid volume estimate. Furthermore, in implementations in which Block S140 converts a pixel-based fluid level measurement into a real fluid volume measurement, Block S140 can further account for an actual or estimated angle between the camera and the canister, actual or estimated distance between the camera and the canister, actual or estimated geometry of the canister (e.g., diameters at the canister base and at the fluid surface), and/or any other relevant metric of or between the canister and the camera.

In one example implementation, Block S110 implements object recognition to determine the particular type of canister in the image, Block S130 identifies a maximum number of pixels between the estimated surface of the fluid and the estimated bottom of the fluid canister, and Block S140 accesses a lookup table for the particular type of canister. The lookup table can correlate a maximum pixel number between the canister bottom and the fluid surface with canister fluid volume such that Block S140 can enter the maximum pixel number calculated in Block S130 and return the fluid volume in the canister.

In another example implementation, Block S120 implements machine vision techniques (e.g., edge detection) to determine the shape and/or geometry of the fluid canister, and Block S130 identifies the maximum number of pixels between the surface of the fluid and the bottom of the fluid canister and converts the pixel number to a physical dimension (e.g., inches, millimeters) of fluid level in the canister. Block S140 subsequently transforms the estimated fluid level into an estimated total fluid volume in the canister according to an estimated physical cross-section of the canister that is based on the determined the shape and/or geometry of the fluid canister from Block S130.

In yet another example implementation, Block S110 implements machine vision techniques to identify fluid level markings printed (or embossed, adhered, etc.) on the fluid canister and Block S130 identifies the surface of the fluid within the canister. Block S140 subsequently extrapolates the volume of fluid within the canister based on the fluid surface and one or more fluid level markings adjacent the fluid surface.

Alternatively, Block S140 can access a direct fluid level measurement from a fluid level sensor coupled to (e.g., arranged in) the fluid canister. Block S140 can also receive manual entry of a manual reading of the fluid level in the canister. For example, the method S100 can implement manual checks to teach or correct automatic fluid volume estimate. Block S140 can thus implement supervised or semi-supervised machine learning to improve canister fluid volume estimation over time. However, Block S140 can function in any other way to estimate or otherwise access a measurement of the volume of fluid in the canister.

Figure 6B:
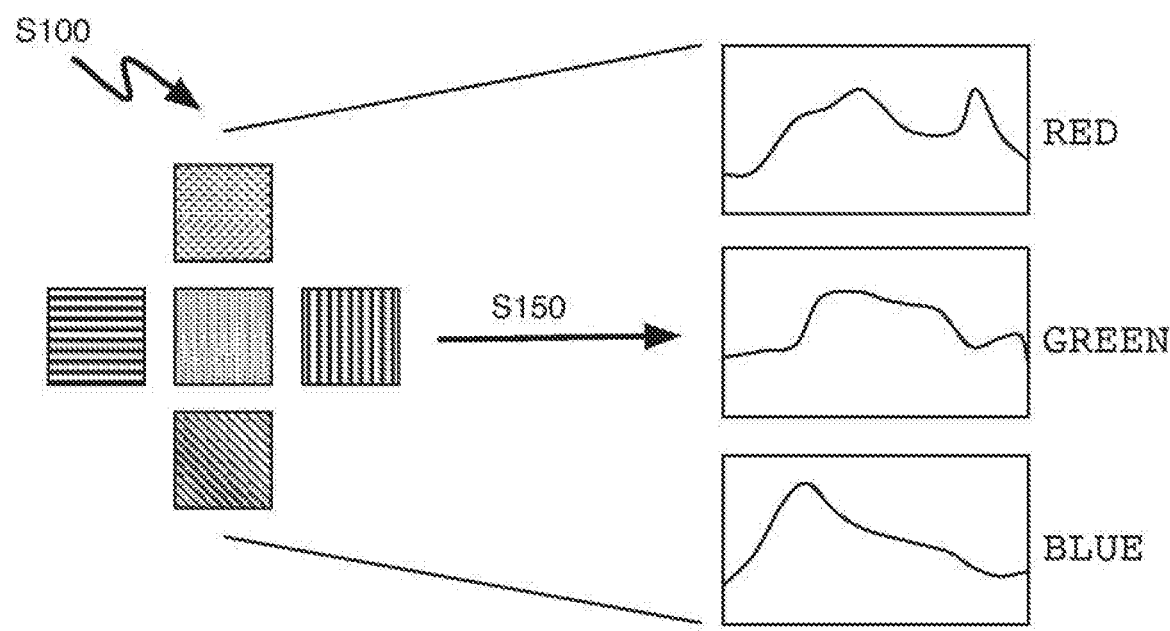

Block S150 of the method S100 recites extracting a feature from the selected area. Generally, Block S150 functions to identify, in the select are of the image of the canister, features indicative of a quality of fluid in the canister. For Block S160 that implements parametric techniques to correlate the extracted featured with a concentration of a blood component within the canister, Block S150 can extract the feature, from one or more pixels within the selected area, that is a color (red), a color intensity (e.g., redness value), a luminosity, a hue, a saturation value, a brightness value, a gloss value, or other color-related value in one or more component spaces, such as the red, blue, green, cyan, magenta, yellow, key, and/or Lab component spaces. Block S150 can additionally or alternatively extract one or more features that is a histogram of various color or color-related values in a set of pixels within the selected area. As shown in FIG. 6B, for Block S160 that implements parametric techniques to correlate the extracted featured with a concentration of a blood component within the canister, Block S150 can extract the feature that is a duster of pixels within the selected area and correlated with a portion of the canister than contains fluid, such as a cluster of pixels that can be compared to template images in a library of template images of known blood component concentrations. However, Block S150 can extract any other suitable feature from one or more pixels within the selected area.

Therefore, as shown in FIGS. 6A and 6B, Block S150 can extract features from multiple pixels within the selected area to collect a set of features indicative of fluid quality over the (full) height, width, and/or area of the select area correlated with a portion of the fluid canister that contains fluid. For example, Block S150 can segment the selected area into m-pixel by n-pixel clusters of pixels, wherein an o by p array of pixel clusters substantially fills the selected area. Block S150 can then analyze each pixel cluster to extract one feature per pixel cluster. Block S150 can further average or otherwise combine features from the pixel clusters to extract a single feature indicative of fluid quality from the selected area. In another example, Block S150 can segment the selected area into non-overlapping single-pixel-thickness (horizontal) rows extending across the full width of the selected area. In this example, Block S150 can average pixel properties in each row to extract a single feature from each row of pixels. Similarly, Block S150 can segment the selected area into three-pixel-thickness row sets extending across the full width of the selected area, wherein the outer single rows of each row set (except the lowermost and uppermost row sets) are shared with adjacent row sets, and wherein the pixels in each row set are averaged to extract a single feature from a set of pixels. Block S150 can additionally or alternatively segment the selected area into non-overlapping triangular pixel clusters, overlapping cross-shaped five-pixel arrays (shown in FIGS. 6A and 6B), overlapping circular pixel dusters, or any other suitable shape and number of overlapping and/or discrete pixel clusters and, from these pixel clusters, extract one or more of the same or different types of features from the set of pixels. Block S150 can alternatively extract a feature from each individual pixel in the selected area or extract any other number of features in any other way from information stored in pixels of the image bounded by the selected area.

Block S150 can additionally or alternatively extract one or more features from the selected area, as described in U.S. patent application Ser. No. 13/544,646, which is incorporated herein in its entirety by the reference. However, Block S150 can function in any other way to extract a feature from the selected area.

As described in U.S. patent application Ser. No. 13/544,646, Block S150 can further access non-image features, such as actual or estimated current patient intravascular hematocrit, estimated patient intravascular hematocrit, historic patient intravascular hematocrit, weight of the fluid canister or direct measurement of canister fluid volume, clinician-estimated canister fluid volume, fluid volumes and/or qualities of previous fluid canisters, previous fluid volumes and/or qualities of the fluid canister, an ambient lighting condition, a type or other identifier of the fluid canister, directly-measured properties of fluid in the fluid canister, a patient vital sign, patient medical history, an identity of a surgeon, a type of surgery or operation in process, or any other suitable non-image feature. For example, as described below and in U.S. patent application Ser. No. 13/544,646, Block S160 and/or other Blocks of the method S100 can subsequently implement any of these non-image features to select template images for comparison with pixel clusters in the selected area, to select of a parametric model or function to transform the extracted feature(s) into a blood component estimate, to define alarm triggers for excess fluid or blood loss, to transform one or more extracted features into a blood quantity indicator, or to transform one or more extracted features into a quantity or quality of an other fluid or solid in the fluid canister. However, the method S100 can implement any of these non-image features to modify, enable, or inform any other function of the method S100.

As shown in FIG. 2, Block S160 of the method S100 recites correlating the extracted featured with a concentration of a blood component within the canister. As shown in FIG. 3, Block S160 can similarly recite correlating the color feature with a concentration of a blood component within the canister. Generally, Block S160 functions to transform one or more features (e.g., color feature) extracted from the image in Block S150 into an estimated concentration of a blood component within fluid in the canister. As described above, the blood component can be any of whole blood, red blood cells, hemoglobin, platelets, plasma, white blood cells, or any other blood component. For example, Block S160 can implement parametric analysis techniques and/or non-parametric analysis techniques, such as described in U.S. patent application Ser. No. 13/544,646, to estimate the concentration of the blood component within the fluid in the canister.

In one implementation, Block S150 extracts features from pixel clusters within the selected area of the image, and Block S160 tags each pixel cluster with a blood volume indicator based on a non-parametric correlation of each pixel cluster with a template image in a library of template images of known blood component concentration. For example, as shown in FIG. 6A, Bock S150 can extract a color intensity in the red component space from a set of pixel clusters, and Block S160 can implement a K-nearest neighbor method to compare each extracted feature with redness intensity values of template images. In this example, each template image can include a pixel cluster tagged with a known fluid quality, such as hemoglobin volume or mass per unit volume of fluid or per pixel unit (e.g., hemoglobin concentration). Each template image can additionally or alternatively include a pixel cluster tagged with the volume, mass, density, etc. per unit volume of fluid or per pixel unit of any other liquid or solid in the canister. Once Block S160 identifies a suitable match between a particular pixel cluster and a particular template image, Block S160 can project known fluid quality information from the particular template image onto the particular pixel cluster. Block S160 can then aggregate, average, and/or otherwise combine pixel cluster tags to estimate output a total blood component concentration for the fluid in the canister. However, Block S160 can correlate the extracted featured with a concentration of a blood component within the canister via any other suitable non-parametric method or technique.

In another implementation, Block S150 extracts features from pixel clusters within the selected area of the image, and Block S160 implements a parametric model or function to tag each pixel cluster with a blood component concentration. As described in U.S. patent application Ser. No. 13/544,646, Block S160 can insert one or more extracted features from one pixel cluster into a parametric function to substantially directly transform the extracted feature(s) from the pixel cluster into a blood component concentration. Block S160 can then repeat this for each other pixel cluster in the selected area. In one example, the extracted feature(s) can include any one or more of a color intensity in the red component space, a color intensity in the blue component space, and/or a color intensity in the green component space. In this example, the parametric function can be a mathematical operation or algorithm that relates color intensity to hemoglobin mass per unit fluid volume. As described in U.S. patent application Ser. No. 13/544,646, reflectance of oxygenated hemoglobin ($HbO_2$) at certain wavelengths of light can be indicative of the concentration of hemoglobin per unit volume of fluid. Therefore, in another example, Block S150 can extract a reflectance values at a particular wavelength for each of a set of pixel clusters in the selected area, and Block S160 can convert each reflectance value into a hemoglobin concentration value by implementing a parametric model. Block S160 can then combine the hemoglobin concentration values to estimate the total (i.e. average) hemoglobin concentration in the canister. Furthermore, because the hemoglobin content of a wet (hydrated) red blood cell is typically about 35%, red blood cell concentration can be extrapolated from the hemoglobin concentration based on a static estimated hemoglobin content (e.g., 35%). Furthermore, Block S150 can access a recent measured hematocrit or estimate a current hematocrit of the patient (as described in U.S. Provisional Application No. 61/646,822), and Block S160 can implement the measured or estimated hematocrit to transform the estimated red blood cell concentration into an estimates extracorporeal blood concentration. However, Block S160 can implement any other parametric and/or non-parametric analysis of single pixels or pixel clusters within the selected area to estimate the concentration of any one or more blood components in fluid within the canister.

Block S170 of the method S100 recites estimating a quantity of the blood component within the canister based on the estimated volume and the concentration of the blood component within the canister. Generally, Block S170 functions to calculate a quantity (e.g., mass, weight, volume, cell count, etc.) of the blood component by multiplying the estimated volume of fluid in the canister by the estimated concentration of the blood component in the fluid in the canister, as shown in FIGS. 7A and 7B. For example Block S170 can estimate a red blood cell count within the canister or a total extracorporeal blood volume in the fluid canister. Block S170 can further interface with a method of U.S. patent application Ser. No. 13/544,646 to combine an estimate blood volume in the canister with estimated blood volumes in surgical gauze sponges, surgical towels, surgical drapes, and/or surgical dressings to estimate total patient blood loss, such as in Block S190 described below. However, Block S170 can function in any other way to estimate a quantity of the blood component within the canister.

As shown in FIG. 3, one variation of the method S100 includes Block S180, which recites extracting a second feature from the selected area, correlating the second extracted featured with a concentration of a non-blood component within the canister, and estimating a quantity of the non-blood component within the canister based on the estimated volume and the concentration of the non-blood component within the canister. Generally, Block S180 implements methods similar to those of Block S150, S160, and/or S170 to estimate a content (e.g., quantity) of a non-blood component within the canister. As described above, the non-blood component can be saline, ascites, bile, irrigant saliva, gastric fluid, mucus, pleural fluid, urine, fecal matter, or any other bodily fluid of a patient, surgical fluid, particulate, or matter in the canister.

In one implementation similar to Blocks S150, S160, and S170 that estimate the blood component content in the fluid canister based on color properties (e.g., 'redness') of the fluid in the fluid canister, Block S180 analyzes other color properties of the fluid to estimate the content of other matter in the canister. For example, Block S180 can analyze the clarity of the fluid in the canister and correlate the estimated clarity of the fluid with a concentration or content of water or saline in the fluid canister. In another example, Block S180 can extract a 'yellowness' (e.g., color intensity in the yellow component space) of the fluid and correlate the yellowness with a concentration or content of plasma and/or urine in the fluid canister. Similarly, Block S150 can extract a 'greenness' (e.g., color intensities in the green and yellow component spaces) of the fluid and correlate the greenness with a concentration or content of bile in the fluid canister. However, Block S180 can estimate the quantity and/or concentration of any other fluid, particulate, or matter in the fluid canister.

Figure 8:
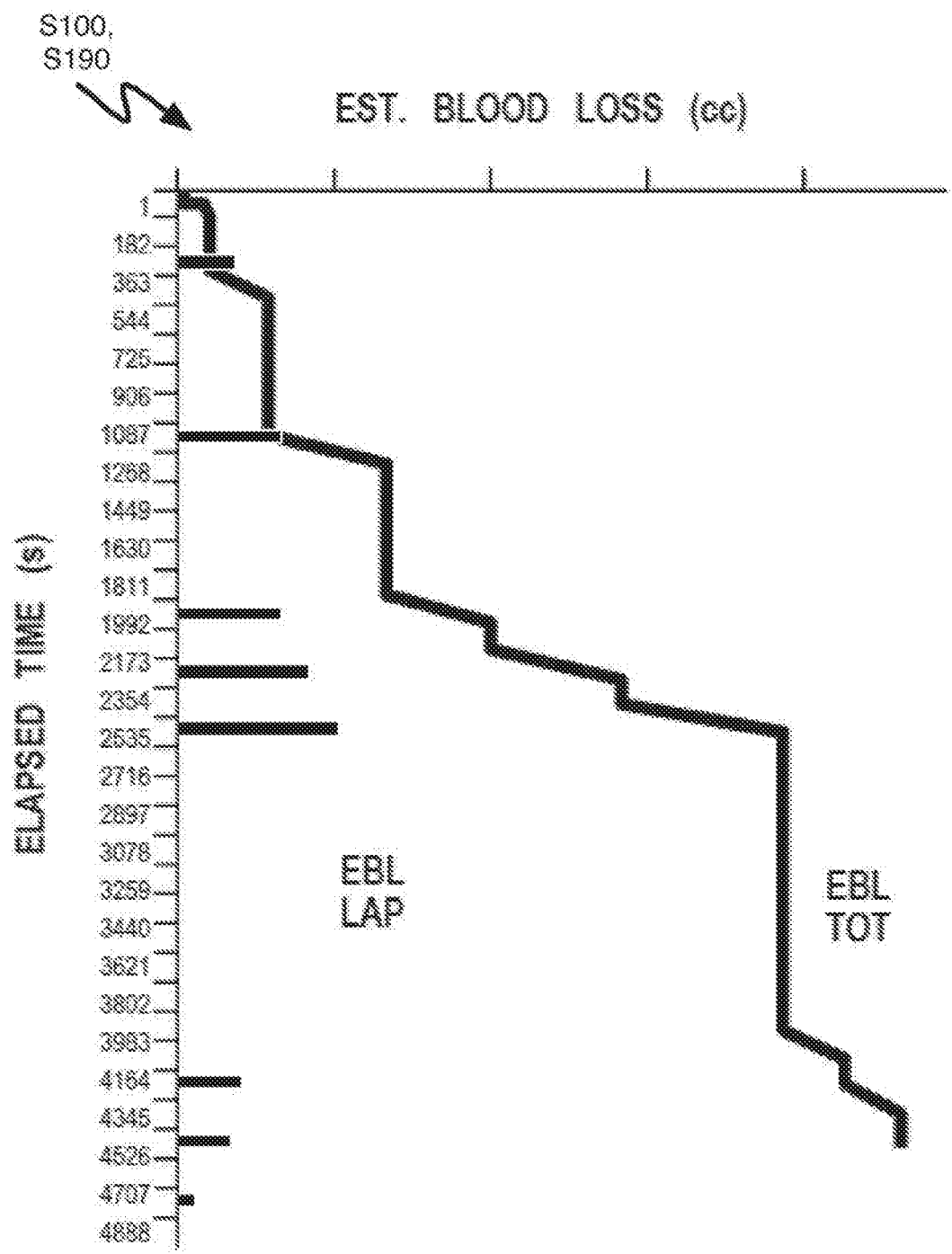
FIG. 8 is a graphical representation in accordance with one variation of the method.

As shown in FIG. 3, one variation of the method S100 includes Block S190, which recites estimating total patient blood loss based on the estimated volume of blood in the canister. For example, Block S190 can sum the estimate blood volume with an estimated blood volume of one or more previous canisters, such as shown in FIG. 8. Furthermore, as described above, Block S190 can combine the canister blood volume estimate of Block S170 with interface with estimated blood volumes in surgical gauze sponges, surgical towels, surgical drapes, and/or surgical dressings as described in U.S. patent application Ser. No. 13/544,646. Block S190 can also add fluid canister blood volume data to a medical record of a patient, trigger an alarm once a threshold extracorporeal blood volume estimate is reached, or estimate current patient hematocrit based on initial patient hematocrit, fluid IVs, transfusions, and total estimated blood loss, such as described in U.S. Provisional Application No. 61/646,822. Block S190 can also estimate a future time at which the patient's intracirculatory blood volume, intracirculatory hematocrit, intracirculatory blood viscosity, and/or intracirculatory red blood cell content, etc. will fall outside of an acceptable window. For example, Block S190 can determine that current total patient blood loss and patient intracirculatory hematocrit are within acceptable bounds but that an increasing blood loss rate will result in excessive blood loss at a particular time in the future (e.g., in approximately five minutes). Block S160 can accordingly determine a future patient need for autologous or allogeneic blood transfusion, a saline drip, etc. based on trends in patient blood-related parameters. Block S190 can therefore estimate patient risk based on estimated blood loss, trigger administration of a blood transfusion once a blood loss threshold is reached, and/or estimate future patient needs or risk based on trends in estimated blood loss. However, Block S190 can function in any other way to maintain a substantially comprehensive estimate of total patient blood (and fluid) loss, such as during a surgery or other medical event.

As shown in FIG. 3, one variation of the method S100 includes Block S192, which recites displaying results of analysis of the canister, such as the total fluid volume, estimated hemoglobin content, red blood cell content, extracorporeal blood volume, etc. in the fluid canister. As shown in FIGS. 1, 7A, and 7B, Block S192 can control an augmented reality overlay on top of a static image or live video feed of the fluid canister also renders on the display. For example, in an implementation in which Blocks of the method S100 are implemented by a mobile computing device (e.g., smartphone, tablet), a display integral with the computing device can display the estimated current blood volume and/or hematocrit quantity in the canister. The display can also render estimated blood volumes and/or hematocrit quantities in the fluid canister over a period of time, a total estimated current blood volume and/or hematocrit quantity in the fluid canister and scanned surgical sponges, and/or past, current, and predicted future total estimated blood volume and/or hematocrit quantities in the fluid canister and scanned surgical sponges. Block S192 can additionally inform a user of a single past fluid quality and/or volume, multiple past fluid qualities and/or volumes, and/or a trend in fluid quality and/or volume over time. However, Block S192 can function to display any relevant fluid canister (and sponge) content information to a user in any other way.

2. Systems

Figure 9:
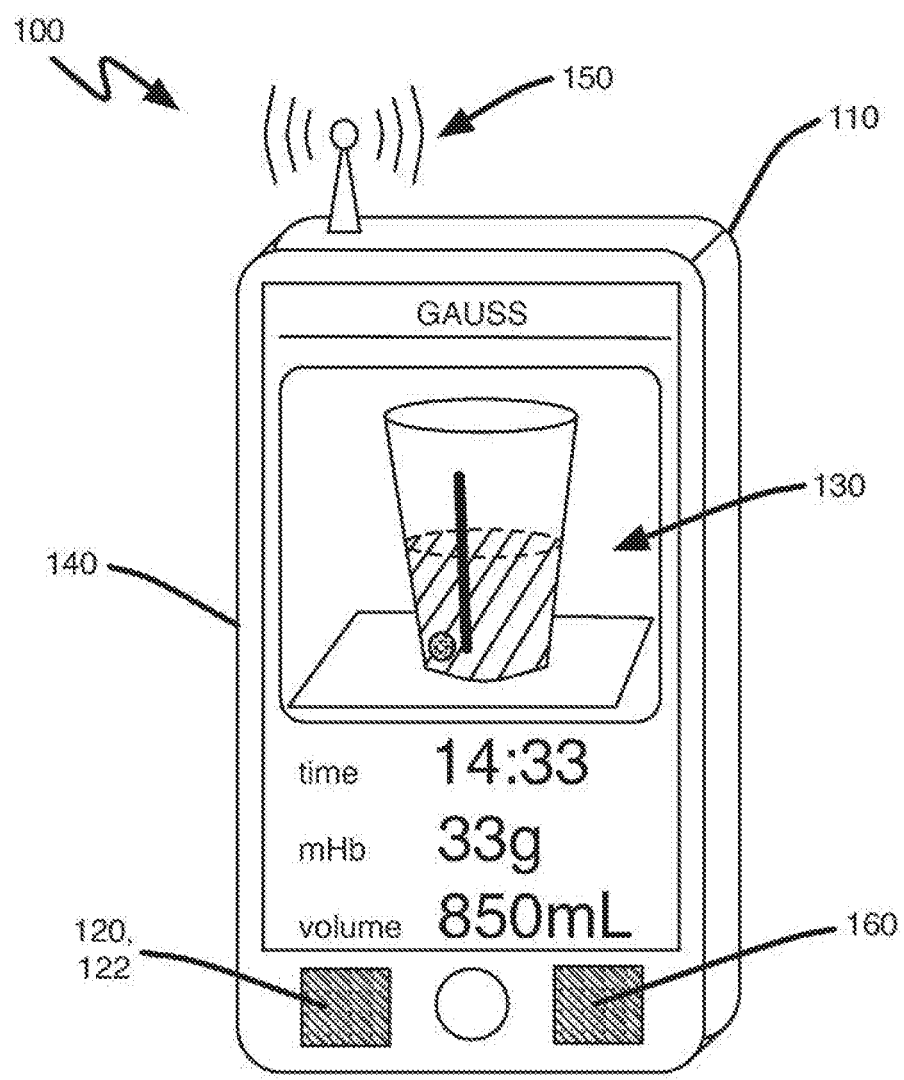
FIG. 9 is a schematic representation of a system of one embodiment.

As shown in FIG. 9, a system 100 for estimating a quantity of a blood component in a fluid canister includes: an optical sensor 110; a processor 120 coupled to the optical sensor 110; a software module 122 executing on the processor 120 and instructing the optical sensor 110 to capture an image of a canister, the software module 122 further instructing the processor 120 to select an area of the image correlated with a portion of the canister containing fluid, to estimate a volume of fluid within the canister based on the selected area, to extract, a feature from the selected area, and to estimate a quantity of a blood component within the canister based on the extracted feature; and a display 130 coupled to the processor 120 and receiving instruction from the software module 122 to display the quantity of the blood component within the canister.

The system 100 functions to implement the method S100 described above, wherein the optical sensor (e.g., camera) implements Block S102 to capture the image of the canister, the processor implements Blocks S110, S120, S130, S140, S150, S160, S170, etc. described above to estimate the quantity and quality of fluid in a surgical suction canister. The system 100, optical sensor, processor, and display can include and/or function as any one or more components described in U.S. patent application Ser. No. 13/544,646. A surgeon, nurse, anesthesiologist, gynecologist, doctor, soldier, or other user can use the system 100 to estimate the quantity and/or quality of a fluid collected in fluid canister, such as during a surgery, child birth, or other medical event. The system 100 can also detect presence of blood in the canister, compute patient blood loss rate, estimate patient risk level (e.g., hypovolemic shock), and/or determine hemorrhage classification of a patient. However, the system 100 can perform any other suitable function.

The system 100 can be configured as a handheld (e.g., mobile) electronic device, such as a smartphone or tablet running an image-based blood estimation application (or app) and including the optical sensor 110, the processor 120, and the display 130. Alternatively, the components of the system 100 can be substantially discreet and distinct (i.e., not contained within a single housing). For example, the optical sensor 110 can be a camera substantially permanently arranged within an operating room, wherein the camera communicates with a local network or a remote server (including the processor 120) on which the image of the canister is analyzed (e.g., according to the method S100), and wherein a display 130 that is a computer monitor, a television, or a handheld (mobile) electronic device accesses and displays the output of the processor 120. However, the system 100 can be of any other form or include any other component.

The system 100 can be used in a variety of settings, including in a hospital setting, such as in a surgical operating room, in a clinical setting, such as in a delivery room, in a military setting, such as on a battlefield, or in a residential setting, such as aiding a consumer in monitoring blood loss due to menorrhagia (heavy menstrual bleeding) or epistaxis (nosebleeds). However, the system 100 can be used in any other setting.

The optical sensor 110 of the system 100 functions to capture the image of the canister. The optical sensor 110 functions to implement Block S102 of the method S100 and can be controlled by the software module 122. In one example implementation, the optical sensor no is a digital camera that captures a color image of the canister or an RGB camera that captures independent image components in the red, green, and blue fields. However, the optical sensor 110 can be any number and/or type of cameras, charge-coupled device (CCD) sensors, complimentary metal-oxide-semiconductor (CMOS) active pixel sensors, or optical sensors of any other type. However, the optical sensor 110 can function in any other way to capture the image of the canister, such as in any suitable form or across any suitable visible or invisible spectrum.

In one implementation, the optical sensor 110 is a camera arranged within a handheld electronic device. In another implementation, the optical sensor no is a camera or other sensor configured to be mounted on a pedestal for placement in an operating room, configured to be mounted to a ceiling over an operating table, configured for attachment to a battlefield helmet of a field nurse, configured to mount to a standalone blood volume estimation system including the processor 120, the display 130, and a staging tray that supports the canister for imaging, or configured for placement in or attachment to any other object or structure.

The software module 122 can also control the optical sensor no, such as by auto-focusing or auto-exposing the optical sensor. Additionally or alternatively, the software module 122 can filter out poor-quality images of the canister and selectively pass high- or sufficient-quality images to the processor 120 for analysis.

According to instructions from the software module 122, the processor 120 of the system 100 receives the image of the canister, estimates a volume of fluid within the canister, extracts a feature from an area of the image correlated with the volume of fluid, correlates the extracted featured with a concentration of a blood component within the canister, and estimates a quantity of the blood component within the canister based on the estimated volume and the concentration of the blood component within the canister. The processor 120 can therefore implement Blocks of the method S100 described above according to instructions from the software module 122. The processor 120 can also analyze different types of images (e.g., static, streaming, .MPEG, .JPG, .TIFF) and/or images from one or more distinct cameras or optical sensors.

The processor no can be coupled to the optical sensor 110, such as via a wired connection (e.g., a trace on a shared PCB) or a wireless connection (e.g., a Wi-Fi or Bluetooth connection), such that the processor 120 can access the image of the canister captured by the optical sensor 110 or visible in the field of view of the optical sensor 110. In one variation, the processor 120 is arranged within a handheld electronic device that also contains the optical sensor no and the display 130. In another variation, the processor 120 is a portion of or is tied to a remote server, wherein image data from the optical sensor 110 is transmitted (e.g., via an Internet or local network connection) to the remote processor 120, wherein the processor 120 estimates the extracorporeal blood volume in at least the portion of the canister by analyzing the image of the canister, and wherein the blood component volume estimate is transmitted to the display 130.

In one implementation and as described above, the processor 120 can pair the portion of the image of the canister to a template image via template matching, and the template image is one template image in a library of template images. For example, the system can further include a data storage module 160 configured to store a library of template images of known concentrations of the blood component. In this implementation, the processor can correlate the extracted featured with the concentration of the blood component by comparing the extracted feature with a template image in the library of template images, as described above. Alternatively and as described above, the processor 120 implements a parametric model to estimate the quantity of the blood component in the canister based on a feature extracted from the image.

The software module 122 of the system 100 functions to control the optical sensor 110, the processor 120, and the display 130 to capture the image of the camera, analyze the image, and display results of the analysis. The software module 122 can execute on the processor as an applet, a native application, firmware, software, or any other suitable form of code to control processes of the system 100. Generally, the software module controls application of Blocks of the method S100 described above, though the software module 122 can control and/or implement any other suitable process or method on or within the system 100.

In one example application, the software module 122 is a native application installed on the system 100 that is a handheld (i.e. mobile) computing device, such as a smartphone or tablet. When selected from a menu within on operating system executing on the computing device, the software module 122 opens, interfaces with a user to initialize a new case, controls the optical sensor 110 integrated into the computing device to capture the image, implements machine vision and executes mathematical algorithms on the processor to estimate the quantity of the blood component, and controls the display 130 to render the estimated quantity of the blood component. However, the software module 122 can be of any other form or type and can be implemented in any other way.

The display 130 of the system 100 depicts the estimated quantity of the blood component in the canister. The display 130 can be arranged within the handheld electronic device (e.g., smartphone, tablet, personal data assistant) that also contains the optical sensor no and the processor 120. Alternatively, the display can be a computer monitor, a television screen, or any other suitable display physically coextensive with any other device. The display 130 can be any of an LED, OLED, plasma, dot matrix, segment, e-ink, or retina display, a series of idiot lights corresponding to estimated quantity of the blood component, or any other suitable type of display. Finally, the display 130 can be in communication with the processor 120 via any of a wired and a wireless connection.

The display 130 can perform at least Block S192 of the method S100 by depicting the estimated quantity of the blood component in the canister and/or in multiple canisters. The blood volume estimate can be depicted in a common form, such as "ccs" (cubic centimeters). As described above, this data can be presented in the form of a dynamic augmented reality overlay on top of a live video stream of the canister that is also depicted on the display 130, wherein images from the optical sensor 110 are relayed substantially in real time, through the processor 120, to the display 130. The data can alternatively be presented in a table, chart, or graph depicting at least one of a time-elapse cumulative estimated quantity of the blood component across multiple samples analyzed over time and individual blood volume estimates for each canister. The display 130 can also render any of a previous image of the canisters, warnings, such as patient risk level (e.g., hypovolemic shock), or a hemorrhage classification of the patient, or suggestions, such as to begin blood transfusion. Any of these data, warnings, and/or suggestions can also be depicted across multiple screens or made available for access on any one of more displays.

One variation of the system 100 further includes a handheld housing 140 configured to contain the optical sensor 110, the processor 120, and the display 130. The handheld housing 140, with optical sensor 110, processor 120, and display 130, can define a handheld (mobile) electronic device capable of estimating blood volume in one or more canisters in any number of suitable environments, such as in an operating room or a delivery room. The housing 140 can be of a medical-grade material such that the system 100 that is a handheld electronic device can be suitable for use in an operating room or other medical or clinical setting. For example, the housing can be medical-grade stainless steel, such as 316L stainless steel, a medical-grade polymer, such as high-density polyethylene (HDPE), or a medical-grade silicone rubber. However, the housing can be of any other material or combination of materials.

In one variation of the system 100, the system 100 further includes a wireless communication module 150 that communicates the estimated quantity of the blood component in the canister to a remote server configured to store an electronic medical record of a patient. The system can also update the medical record with estimated blood loss over time, patient risk level, hemorrhage classification, and/or other blood-related metrics. The patient medical record can therefore be updated substantially automatically during a medical event, such as a surgery or childbirth.

The systems and methods of the preferred embodiments can be embodied and/or implemented at least in part as a machine configured to receive a computer-readable medium storing computer-readable instructions. The instructions are executed by computer-executable components integrated with the system, the optical sensor, the processor, the display, hardware/firmware/software elements of a system or handheld computing device, or any suitable combination thereof. Other systems and methods of the preferred embodiments can be embodied and/or implemented at least in part as a machine configured to receive a computer-readable medium storing computer-readable instructions. The instructions are executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is a processor but any suitable dedicated hardware device can (alternatively or additionally) execute the instructions.

As a person skilled in the art of estimating the extracorporeal blood volume in a canister will recognize from the previous detailed description and from the figures and claims, modifications and changes can be made to the preferred embodiments of the invention without departing from the scope of this invention defined in the following claims.

We claim:

1. A method for assessment of blood within a canister, comprising:
- at a processor, selecting an area of an image of the canister upon detection of a reference marker on the canister;
- at the processor, determining a fluid level within the canister based upon the area within the image;
- at the processor, generating an estimated volume of blood within the canister based on the fluid level;
- at the processor, extracting a feature from at least one pixel of the area;
- at the processor, correlating the feature with a concentration, of a blood component within the canister;
- at the processor, estimating a quantity of the blood component within the canister based on the estimated volume and the concentration of the blood component within the canister; and
- by way of the processor, rendering an analysis indicative of the quantity of the blood component and an estimated total patient blood loss, based upon the estimated volume of blood within the canister.

* * * * *

UNITED STATES PATENT AND TRADEMARK OFFICE
CERTIFICATE OF CORRECTION

PATENT NO. : 10,706,541 B2
APPLICATION NO. : 16/392345
DATED : July 7, 2020
INVENTOR(S) : Satish et al.

Page 1 of 1

It is certified that error appears in the above-identified patent and that said Letters Patent is hereby corrected as shown below:

In the Specification

Column 8, Line 13, delete "Bock" and insert --Block-- therefor

Column 9, Line 12, delete "dusters" and insert --clusters-- therefor

Column 9, Line 59, delete "8100" and insert --S100-- therefor

Column 11, Line 9, delete "duster" and insert --cluster-- therefor

Column 11, Line 43, delete "dusters," and insert --clusters,-- therefor

Column 12, Line 40, delete "Bock" and insert --Block-- therefor

Column 16, Line 16, delete "no" and insert --110-- therefor

Column 16, Line 29, delete "no" and insert --110-- therefor

Column 16, Line 39, delete "no," and insert --110,-- therefor

Column 16, Line 59, delete "no" and insert --120-- therefor

Column 16, Line 66, delete "no" and insert --110-- therefor

Column 17, Line 54, delete "no" and insert --110-- therefor

Signed and Sealed this
Nineteenth Day of January, 2021

Andrei Iancu
*Director of the United States Patent and Trademark Office*